United States Patent
Melis et al.

(10) Patent No.: US 7,745,696 B2
(45) Date of Patent: Jun. 29, 2010

(54) **SUPPRESSION OF *TLA1* GENE EXPRESSION FOR IMPROVED SOLAR CONVERSION EFFICIENCY AND PHOTOSYNTHETIC PRODUCTIVITY IN PLANTS AND ALGAE**

(75) Inventors: Anastasios Melis, El Cerrito, CA (US); Mautusi Mitra, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 927 days.

(21) Appl. No.: 11/423,620

(22) Filed: Jun. 12, 2006

(65) Prior Publication Data

US 2008/0120749 A1    May 22, 2008

(51) Int. Cl.
*C12N 15/11* (2006.01)
*C12N 15/29* (2006.01)
*C12N 15/82* (2006.01)

(52) U.S. Cl. .................. 800/285; 800/286; 800/296

(58) Field of Classification Search ............... None
See application file for complete search history.

(56) References Cited

OTHER PUBLICATIONS

Wu K. et al., Plant Physiology, 1997, vol. 114, pp. 1421-1431.*
Waterhouse P. et al., Trends in Plant Sciences, Nov. 1999, vol. 4, No. 11 pp. 452-457.*
Branch A.D. TIBS, Feb. 1998, pp. 45-50.*
Polle, J. et al. Planta (2003) vol. 217: pp. 49-59.*
Kanakagiri, S., et al., "*Chlamydomonas reinhardtii* TLA1 nuclear gene for the regulation of photosystem chlorophyll antenna size in photosynthesis, complete cds., (bases 1 to 2181)," GenBank Accession No. AF534570, 3 pgs. (2002).
Kanakagiri, S., et al., "*Chlamydomonas reinhardtii* chlorophyll antenna size regulatory protein (TLA1) mRNA, complete cds.," GenBank Accession No. AF534571, 3 pgs, (2002).
Melis, A., "Spectroscopic methods in photosynthesis: photosystem stoichiometry and chlorophyll antenna size," *Phil. Trans. R. Cos. Lond., Series B, Biological Sciences*, vol. 323, pp. 397-409 (1989).
Melis, A., "Bioengineering of Green Algae to Enhance Photosynthesis and Hydrogen Production," *Artificial Photosynthesis: From Basic Biology to Industrial Application*, Chapter 12, pp. 229-240 (2005).
Polle, J., et al., "tla1, a DNA insertional transformant of the green alga *Chlamydomonas reinhardtii* with a truncated light-harvesting chlorophyll antenna size," *Planta*, vol. 217, pp. 49-59 (2003).

* cited by examiner

*Primary Examiner*—Russell Kallis
(74) *Attorney, Agent, or Firm*—Townsend and Townsend and Crew LLP

(57) ABSTRACT

The invention provides method and compositions to minimize the chlorophyll antenna size of photosynthesis by decreasing TLA1 gene expression, thereby improving solar conversion efficiencies and photosynthetic productivity in plants, e.g., green microalgae, under bright sunlight conditions.

23 Claims, 14 Drawing Sheets

Fig. 4

5' RACE from WT

GATGTCGTGTTGACTTTGCGTTACAACCGTGAAGTATATTAGAACTCATTTGCCTGCCACAACCTCAGAC
CAAGAGACGCGCGAAAAACTGACACGATGACTTTCAGCTGCTCCGCTGACCAAACCGCGCTCTTAAAGAT
TCTTGCACACGCGGCTAAGTATCCATCAAATAGCGTGAATGGTGTCCTCGTCGGGACAGCGAAGGAGGGC
GGCTCTGTCGAAATCCTGGACGCGATTCCACTGTGTCACACGACGCTGACCCTGGCGCCAGCACTGGAGA
TAGGTCTCGCCCAGGTGGAGTCCTACACGCATATCACGGGCAGCGTGGCGATTGTGGGCTACTACCAATC
AGACGCACGTTTCGGCCCCGGG

5' RACE from *tla1* acgccatagtgactggcgatgctgtcg
gaatggacgatatcccgcaagaggcccggcagtaccggcataaccaagcctatgcctacagcat
ccagggtgacggtgccgaggatgacgatgagcgcattgttagattccatacacggtgcctgact
gcgttagcaatttaactgtgataaactaccgcATGACTTTCAGCTGCTCCGCTGACCAAACCGCGCTCTT
AAAGATTCTTGCACACGCGGCTAAGTATCCATCAAATAGTGTGAATGGTGTCCTCGTCGGGACAGCGAAG
GAGGGCGGCTCTGTCGAAATCCTGGACGCGATTCCACTGTGTCACACGACGCTGACCCTGGCGCCAGCAC
TGGAGATAGGTCTCGCCCAGGTGGAGTCCTACACGCATATCACGGGCAGCGTGGCGATTGTGGGCTACTA
CCAATCAGACGCACGTTTCGGCCCCGGG 3'End of pJD67 sequence CGGCACCAGCAAGCGCTCGGTGCTGGAGCAGGTGCAGAAGATGCGCACCTACCTGGCGGCGGAGGGACAG
CACTGAGCGGGTCGGGGGAGGGGGGCGGGTGTGTATGTGTGTGTGTGTGCGTGTGTAAGTCTCGGTGGA
GGGGTGGTCCTCTATATGGCGGCGGGGCCACAGGGGGACGGGTGTGACAGAGTTACGGCCGGCAGCCAGCG
GAGTCCCGGGATGGATTAAGGATCCacaggacgggtgtggtcgccatgatcgcgtagtcgatagtggctc
caagtagcgaagcgagcaggactgggcggcggccaaagcggtcggacagtgctccgagaacgggtgcgca
tagaaattgcatcaacgcatatagcgctagcagc<u>acgccatagtgactggcgatgctgtcggaatggacg
atatcccgcaagaggcccggcagtaccggcataaccaagcctatgcctacagcatccagggtgacggtgc
cgaggatgacgatgagcgcattgttagatttcatacacggtgcctgactgcgttagcaatttaactgtga
taaactaccgc</u> attaaagct

Fig. 12A

```
C. reinhardtii     --MT----FSCSADQTALLKILAHAAKYPSNSVNGVLVGTAKE-----GGSVEILDAIPL
A. thaliana        MGMGSNGELKYEISQNAYIKLVLHSLRHKTAAVNGVLVGRISP---KDDGVVEISDSVPL
O. sativa          --MG--AECKYEVAQVAYVKLALHALKHPAAAVNGLLVGRLLDGAASPAAVVSIADAVPL
H. sapiens         --MG-----EVEISALAYVKMCLHAARYPHAAVNGLFLAPAPR----SGEGLCLTDCVPL
D. melanogaster    --MC-----DYKVSERAYAKLIFHAAKYPHQAVNGLLLAEKTS----KGSQVEIVDAIPL
                     *     .  .    *:  *: ::    :***::: .         : : *.:**

C. reinhardtii     CHT--TLTLAPALEIGLAQVESYTHITGSVAIVGYYQSDARFGPGDLPPL-GRKIADKVS
A. thaliana        FHS--NLALLPPLEISLIMIEEHYVAQG-LSIVGYFHANERFDDVELCGV-AKNIGDHIS
O. sativa          SHHPHHLPLLPTLELALTLVEDHFAAQG-LAVVGYYHANARRDDADLPPV-AKRVGDHVF
H. sapiens         FHS--HLALSVMLEVALNQVDVWGAQAG-LVVAGYYHANAAVNDQSPGPL-ALKIAGRIA
D. melanogaster    FHQ--CLYVTPMAEVALMLIDAHAEREG-LVIAGYYAAPENFYDNQVDKTPAAKIADKIQ
                    *    *  :   *:.*  ::     *   : :.**: :    .    .  .:..::

C. reinhardtii     EHQAQAVVLVLDNKRLEQFCKAQADNP-FELFSKDGSKGWKRASADGG-ELALKNADWKK
A. thaliana        RYFPQAPILLLNNKKLEALSKGKERSPVMQLCVKDASKNWRVVGADGGSKLLLKEPSANV
O. sativa          RNFPRAAVLLLDNKKLEEAVKGKSREPVVQLYTRDSSKSWRQAGSDGSSQLTLKEPSTNM
H. sapiens         EFFPDAVLIMLDNQKLVP----QPRVPPVIVLENQGLR-W--VPKDKNLVMWRDWEESRQ
D. melanogaster    ENFKNACFVVVDN-KLMTLQHDRAAIQVFNCPGDSGAR-W------SKAKFTLSQASDTL
                    .    *  .:::* :*       :         ..  :   *       :   .

C. reinhardtii     LREEFFVMFKQLKHRTLHDFEEHLDDAGKDWLNKGFASSV-KFLLP----GNAL
A. thaliana        VLSDYISSE---KWKDVTDVDDHLDDVTKDWLNPGLFN--------------
O. sativa          VLADHVTTK---KWQQVVDFDDHLDDISKDWLNPGLLA--------------
H. sapiens         MVGALLEDR---AHQHLVDFDCHLDDIRQDWTNQRLNTQITQWVGPTNGNGNA-
D. melanogaster    EGVSLLLKRG--AMRDLVDFDNHLDNPDKNWTNDFLNQPLNDLQKLY-------
                              :   : *.: ***:   ::* *     :
```

Fig. 13

Examples of Tla1 protein sequence alignment in plants and algae

```
Oryza          --MG--AECKYEVAQVAYVKLALHALKHPAAAVNGLLVGRLLDGAASPAAVVSIADAVPL 56
Zea            --MG--AECRYEVAQAAYIKLALHALKHPATAVNGLLVGRLVEPSSSP-AVVSVIDAVPL 55
Arabidopsis    MGMGSNGELKYEISQNAYIKLVLHSLRHKTAAVNGVLVGRIS---PKDDGVVEISDSVPL 57
Chlamydomonas  ------MTFSCSADQTALLKILAHAAKYPSNSVNGVLVGTAK-----EGGSVEILDAIPL 49
                       . * * :*:  *: :: : :***:***        . *.: *::**

Oryza          SHHPHHLPLLPTLELALTLVEDHFAAQG--LAVVGYYHANARRDDADLPPVAKRVGDHVF 114
Zea            SHHPHHLPLLPTLELALTLVEDHFATQGEGLAVVGYYHANPRCDDTELPPVAKRVGDHIF 115
Arabidopsis    FHS--NLALLPPLEISLIMIEEHYVAQG--LSIVGYFHANERFDDVELCGVAKNIGDHIS 113
Chlamydomonas  CHT--TLTLAPALEIGLAQVESYTHITG-SVAIVGYYQSDARFGPGDLPPLGRKIADKVS 106
                *    *.* *.**:.*  :*.:    *   :::***:::  *  .  :*   :.:.*::

Oryza          RNFPRAAVLLLDNKKLEEAVKGKSREPVVQLYTRDSSKSWRQAGSDGSSQLTLKEPSTNM 174
Zea            RYFPRSAVLLVDNKKLEEAVKGKFSDAVIQLHTRDSSKSWRQAGSDGSSQLILKEPSTNV 175
Arabidopsis    RYFPQAPILLLNNKKLEALSKGKERSPVMQLCVKDASKNWRVVGADGGSKLLLKEPSANV 173
Chlamydomonas  EHQAQAVVLVLDNKRLEQFCKAQADN-PFELFSKDGSKGWKRASADGG-ELALKNADWKK 164
                 . .::  :*:::**:**  *.:    .:*  :*.**.*:  ..:**. :* **:.. :

Oryza          VLADHVTTK---KWQQVVDFDDHLDDISKDWLNPGLLA----------- 209
Zea            VLADHVTTK---KWEKIVDFDDHLDDISKDWSNPGLLD----------- 210
Arabidopsis    VLSDYISSE---KWKDVTDVDDHLDDVTKDWLNPGLFN---------- 208
Chlamydomonas  LREEFFVMFKQLKHRTLHDFEEHLDDAGKDWLNKGFASSVKFLLPGNAL 213
                :  :..    * . : *.::****  *** * *:
```

Conserved domains in the *Chlamydomonas reinhardtii* Tla1 protein are defined by the following amino acid numbers:

Domain A: amino acid positions 9-33 (QTALLKILAHAAKYPSNSVNGVLVG)
Domain B: amino acid positions 41-70 (VEILDAIPLCHTTLTLAPALEIGLAQVESY)
Domain C: amino acid positions 75-129
    (GSVAIVGYYQSDARFGPGDLPPLGRKIADKVSEHQAQAVVLVLDNKRLEQFCKAQ)
Domain D: amino acid positions 135-163 (ELFSKDGSKGWKRASADGG-ELALKNADWK)
Domain E: amino acid positions 177-200 (KHRTLHDFEEHLDDAGKDWLNKGF)

SUPPRESSION OF *TLA1* GENE EXPRESSION FOR IMPROVED SOLAR CONVERSION EFFICIENCY AND PHOTOSYNTHETIC PRODUCTIVITY IN PLANTS AND ALGAE

STATEMENT AS TO RIGHTS TO INVENTIONS MADE UNDER FEDERALLY SPONSORED RESEARCH AND DEVELOPMENT

This invention was made with Government support under Grant (Contract) Nos. DE-FC36-00GO10536 and DE-FG36-05GO15041 awarded by the United States Department of Energy. The Government has certain rights in this invention.

BACKGROUND OF THE INVENTION

Oxygenic photosynthesis depends on the absorption of sunlight by auxiliary light-harvesting pigments, which are incorporated within the holocomplexes of photosystem-I and photosystem-II. In each photosystem (PS), sizable arrays of chlorophylls and other accessory pigments (e.g., carotenoids) act cooperatively as antennae for the collection of light energy and as a conducting medium for excitation migration toward a photochemical reaction center (see, e.g., Emerson & Arnold, *J Gen Physiol* 15: 391-420, 1932; Emerson & Arnold, *J Gen Physiol* 16: 191-205, 1933; Gaffron & Wohl, *Naturwissenschaften* 24: 81-90, 1936; Melis, In, *Oxygenic Photosynthesis: The Light Reactions*" (DR Ort, CF Yocum, eds), Kluwer Academic Publishers, Dordrecht, The Netherlands, pp. 523-538, 1996). Organized as distinct pigment-protein complexes and contained within PSI and PSII, these light-harvesting antennae perform the functions of light absorption and excitation energy transfer to a photochemical reaction center (see, e.g., Simpson and Knoetzel, In: Ort DR and Yocum CF (eds), *Oxygenic Photosynthesis: The Light Reactions*, pp. 493-506, Kluwer Academic Publishers, Dordrecht, The Netherlands, 1996; Pichersky and Jansson, In: Ort DR and Yocum CF (eds), *Oxygenic Photosynthesis: The Light Reactions*, pp. 507-521, Kluwer Academic Publishers, Dordrecht, The Netherlands, 1996). Up to 350 chlorophyll a (Chl a) and Chl b molecules can be found in association with PSII, whereas the Chl antenna size of PSI may contain up to 300 mainly Chl a molecules (Melis, *Biochim. Biophys. Acta* (Reviews on Bioenergetics) 1058: 87-106, 1991; Melis, In, *Oxygenic Photosynthesis: The Light Reactions*" (DR Ort, CF Yocum, eds), Kluwer Academic Publishers, Dordrecht, The Netherlands, pp. 523-538, 1996). Some of these Chl molecules are contained within the PS-core complexes, which are highly conserved in all organisms of oxygenic photosynthesis. The PSII-core complex contains about 37 Chl a molecules, whereas the PSI-core complex contains 95 Chl a molecules (Glick & Melis, *Biochim Biophys Acta* 934: 151-155, 1988; Jordan et al., *Nature* 411(6840): 909-917, 2001; Zouni et al., *Nature* 409: 739-743, 2001; Ruban et al., *Nature* 421: 648-652, 2003). In green plants and algae, the remaining Chl a and Chl b antenna molecules are organized within 10 peripheral subunits of the so-called auxiliary chlorophyll a-b light-harvesting complex. There are six such subunits for PSII (Lhc b1-b6) and four for PSI (Lhc a1-a4) (Jansson et al., *Plant Mol Biol Rep*, 10: 242-253, 1992). These peripheral Lhc subunits are not essential for the process of photosynthesis. Indeed, when the chloroplast development is limited, stable assembly of the PSII-core and PSI-core complexes takes place in the absence of any Lhc proteins (Glick & Melis, 1988, supra).

A genetic tendency of photosynthetic organisms to assemble large arrays of light absorbing Chl antenna molecules in their photosystems is a survival strategy and a competitive advantage in the wild, where light is often limiting (Kirk, *Light and photosynthesis in aquatic ecosystems*, 2nd edn. Cambridge University Press, Cambridge, England, 1994). However, the Chl antenna size of the photosystems is not fixed but can vary substantially depending on developmental, genetic, physiological and even environmental conditions (Melis, 1991, supra). It is recognized in the field that a genetic regulatory mechanism dynamically modulates the Chl antenna size of photosynthesis (Anderson, *Annu Rev Plant Physiol* 37: 93-136, 1986; Escoubas et al., *Proc. Nat. Acad. Sci.* 92: 10237-10241, 1995; Melis, 1991 and 1996, both supra; Melis, *Intl. J. Hydrogen Energy* 27: 1217-1228, 2002; Melis, Chapter 12 in *Artificial Photosynthesis: From Basic Biology to Industrial Application*, A F Collins and C Critchley (eds.), Wiley-Verlag & Co., pp. 229-240, 2005). For example, the Chl antenna size is adjusted and optimized in response to the light intensity during plant growth (Ley and Mauzerall, *Biochim Biophys Acta* 680: 95-106, 1982; Sukenik et al., *Biochim Biophys Acta* 932: 206-215, 1988; Smith et al., *Plant Physiol.* 93: 1433-1440, 1990; LaRoche et al., *Plant Physiol* 97: 147-153, 1991; Maxwell et al., *Plant Physiol* 107: 687-694, 1995; Falbel et al., *Plant Physiol.* 112: 821-832, 1996; Webb and Melis, *Plant Physiol.* 107: 885-893, 1995; Ohtsuka et al., *Plant Physiol.* 113: 137-147, 1997; Tanaka and Melis, *Plant Cell Physiol.* 38: 17-24, 1997; Masuda et al., *Plant Physiol.* 128: 603-614, 2002). Physiological and biochemical consequences of the function of this molecular regulatory mechanism for the Chl antenna size are well understood. However, little is known about the genes and proteins and their mode of action in this regulation. The Chl antenna size regulatory mechanism is highly conserved and functions in all organisms of oxygenic and anoxygenic photosynthesis (Anderson, *Annu Rev Plant Physiol* 37: 93-136, 1986; Nakada et al., *J Ferment Bioengin* 80: 53-57, 1995; Escoubas et al., *Proc. Nat. Acad. Sci.* 92: 10237-10241, 1995; Huner et al., *Trends in Plant Science*, 3: 224-230, 1998; Yakovlev et al., *FEBS Lett* 512: 129-132, 2002; Masuda et al., *Plant Physiol.* 128: 603-614, 2002; Masuda et al., *Plant Mol. Biol.* 51: 757-771, 2003). Thus, identification of the relevant genes and elucidation of the genetic mechanism for the regulation of the Chl antenna size in *Chlamydomonas reinhardtii* can apply to all photosynthetic organisms.

Although a smaller Chl antenna size may compromise the ability of a plant, e.g., algae, to survive in the wild, in a high-density cultivation environment, a smaller chlorophyll antenna size would help to diminsh the over-absorption and wasteful dissipation of excitation energy by the first layer of leaves, cells or chloroplasts, and would also help diminish photoinhibiton of photosynthesis at the surface while permitting greater transmittance of light deeper into the culture. Such altered optical properties of the cells would result in greater photosynthetic productivity and enhanced solar conversion efficiency by the high-density culture.

Previous work (Masuda et al. 2003, supra; Polle et al., *Planta* 217: 49-59, 2003, Melis, 2005, supra) described the isolation of tla1, a *Chlamydomonas reinhardtii* DNA insertional mutant having a truncated light-harvesting chlorophyll antenna size (Polle et al, 2003, supra). Although these studies identified a mutant that had reduced antenna size, there was no teaching of whether the phenotype was associated with increased or suppressed tla1 expression. Accordingly, there is a need for further elucidation of mechanism of Tla1-mediated changes in chlorophyll antenna size.

BRIEF SUMMARY OF THE INVENTION

The current invention is based on the discovery that suppression of Tla1 expression results in reduced chlorophyll antenna size. Thus, in one aspect, the invention provides a method of decreasing chlorophyll antenna size in a plant, e.g., green algae, the method comprising: inhibiting expression of a Tla1 nucleic acid in the plant by introducing into the plant an expression cassette comprising a promoter operably linked to a polynucleotide, or a complement thereof, that specifically hybridizes to a nucleic acid that has at least 70% identity, often at least 80%, 90%, or 95% identity, to at least 200 contiguous nucleotides of a sequence encoding SEQ ID NO:2; and selecting a plant with decreased chlorophyll antenna size compared to a plant in which the expression cassette has not been introduced. The promoter may be inducible or constitutive. In some embodiments the polynucleotide is operably linked to the promoter in the antisense orientation; in other embodiments, the polynucleotide is operably linked to the promoter in the sense orientation.

In some embodiment, the polynucleotide introduced into the plant, e.g., green algae, is an siRNA. In other embodiments, the polynucleotide is an antisense RNA.

The nucleic acid to which the polynucleotide hybridizes can encode a polypeptide of SEQ ID NO:2. In particular embodiments, the nucleic acid is SEQ ID NO:3 or SEQ ID NO:1.

Often the plant, e.g., green algae, into which the nucleic acid is introduced, is selected from *Chlamydomonas reinhardtii, Scenedesmus obliquus, Chlorella vulgaris, Botryococcus braunii, Botryococcus sudeticus, Dunaliella salina*, or *Haematococcus pluvialis*.

The invention also provides a plant comprising an expression cassette comprising a polynucleotide, or a complement thereof, that specifically hybridizes to a nucleic acid that has at least 70% percent identity, often at least 80%, 90%, or 95% identity, to at least 200 contiguous nucleotides of a sequence encoding SEQ ID NO:2. In preferred embodiments, the plant is a green algae, e.g., *Chlamydomonas reinhardtii, Scenedesmus obliquus, Chlorella vulgaris, Botryococcus braunii, Botryococcus sudeticus, Dunaliella salina*, or *Haematococcus pluvialis*.

The invention additionally provides a method of enhancing yields of photosynthetic productivity under high-density growth conditions, the method comprising cultivating a Tla1-suppressed plant of the invention, e.g., green algae such as *Chlamydomonas reinhardtii, Scenedesmus obliquus, Chlorella vulgaris, Botryococcus braunii, Botryococcus sudeticus, Dunaliella salina*, or *Haematococcus pluvialis*, under bright sunlight and high density growth conditions.

Additionally, the invention provides a method of enhancing $H_2$ production, the method comprising suppressing Tla1 gene expression in a green algae, e.g., *Chlamydomonas reinhardtii, Scenedesmus obliquus*, or *Chlorella vulgaris*, to be used for $H_2$ production; and cultivating the algae under conditions in which $H_2$ is produced.

The invention further provides a method of enhancing bio-oil or bio-diesel production, the method comprising suppressing Tla1 gene expression in a green algae, e.g., *Botryococcus braunii* or *Botryococcus sudeticus* to be used for bio-oil or bio-diesel production; and cultivating the algae under conditions in which bio-oil or bio-diesel is produced.

Further, the invention provides a method of enhancing beta-carotene, lutein or zeaxanthin production, the method comprising suppressing Tla1 gene expression in a green algae, e.g., *Dunaliella salina*, to be used for beta-carotene, lutein or zeaxanthin production; and cultivating the algae under conditions in which beta-carotene, lutein or zeaxanthin is produced.

In other embodiments, the invention provides a method of enhancing astaxanthin production, the method comprising suppressing Tla1 gene expression in a green algae, e.g., *Haematococcus pluvialis*, to be used for astaxanthin production; and cultivating the algae under conditions in which astaxanthin is produced.

In another aspect, the invention provides a method of screening for plants, preferably, green algae, that show enhanced yield of photosynthetic productivity, the method comprising: introducing a mutation into a population of plants, e.g., green algae; and screening for inhibition of Tla1 gene expression, wherein inhibition of Tla1 gene expression is determined by measuring the level of Tla1 mRNA or Tla1 protein. Preferably the plants, e.g., green algae, are selected from *Chlamydomonas reinhardtii, Scenedesmus obliquus, Chlorella vulgaris, Botryococcus braunii, Botryococcus sudeticus, Dunaliella salina*, or *Haematococcus pluvialis*.

BRIEF DESCRIPTION OF THE DRAWINGS

FIG. 4. 5' RACE DNA sequence analysis of wild type (cw15) and tla1 mutant and sequence comparison with the 3' end of pJD67. Upper panel: DNA sequence obtained from the 5' RACE of the wild type (SEQ ID NO:16). Unshaded nucleotides represent the 5' UTR of the cDNA sequence amplified from the WT-Tla1 gene transcripts. The ATG start codon is denoted in bold characters. Exon 1 nucleotides are shown in shaded upper case characters. Middle panel: DNA sequence obtained from the 5' RACE of the tla1 mutant (SEQ ID NO:17). The underlined lower case letters represent the apparent 5' UTR sequence amplified from the tla1 mutant. Exon 1 nucleotide sequences are shown in shaded upper case characters. Lower panel: 3' end DNA sequence of plasmid pJD67 (SEQ ID NO:18). Shaded upper case characters correspond to the DNA sequence of the ARG7.8 gene, whereas lower case characters correspond to the 3' end of the vector sequence. Rearrangements in that portion of the plasmid are shown in bold characters, as follows: the last 9 plasmid bases "a t t a a a g c t" were deleted during the plasmid insertion.

FIG. 13 shows an alignment of Tla1 protein sequences (SEQ ID NOS:20,23,19 and 2, respectively) in plants and algae. Conserved domains in C. reinhardtii Tla1 protein× SEQ ID NOS:24-28.

DETAILED DESCRIPTION OF THE INVENTION

Definitions

Figure 1:
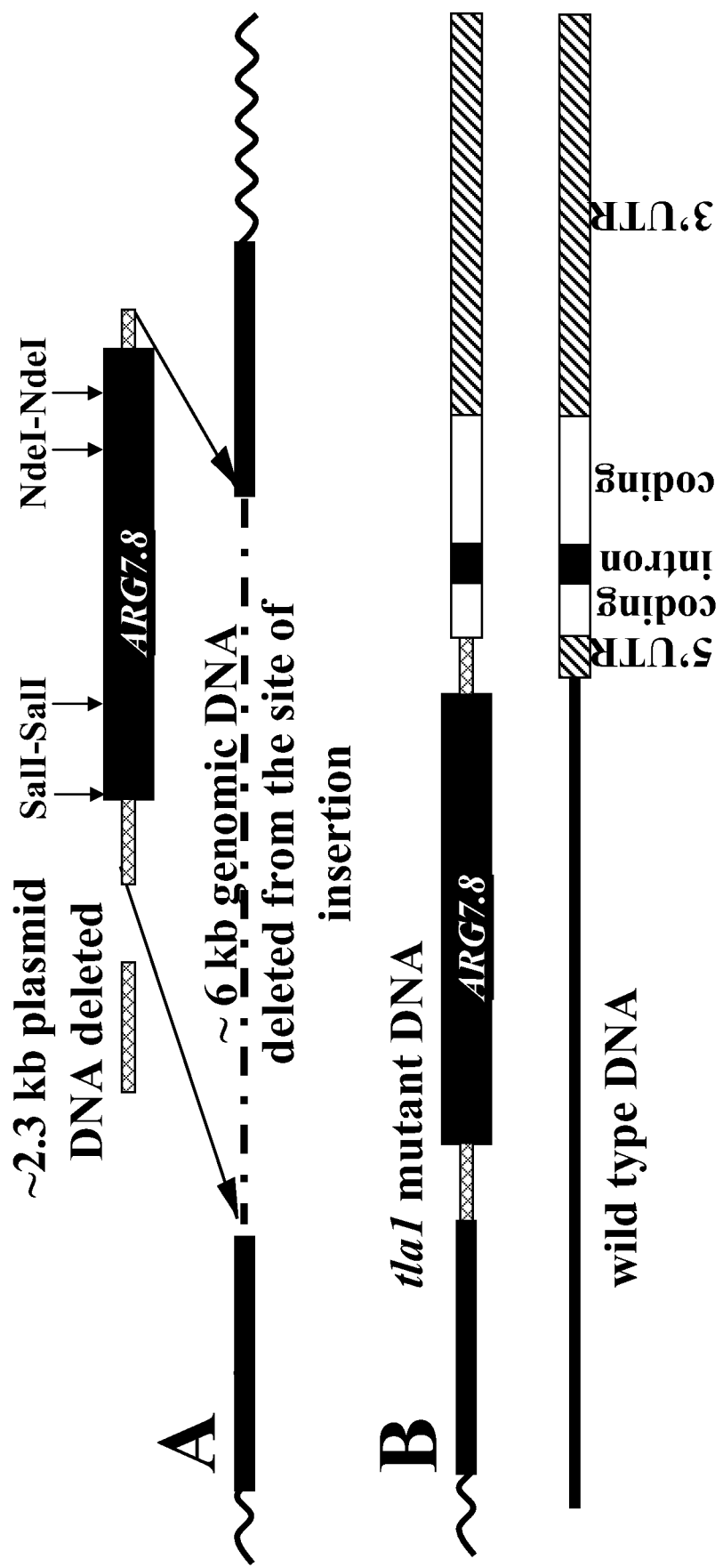
FIG. 1. (A) Map of plasmid pJD67 insertion in the tla1 mutant genomic DNA. There is a single plasmid insert, containing the ARG7.8 gene. An approximately 2.3 kb segment of the 5' end and 9 base pairs at the 3' end of the pJD67 were deleted upon plasmid insertion. About 6 kb of *C. reinhardtii* genomic DNA in the tla1 mutant was also deleted from the site of plasmid insertion. Probes for screening tla1 partial genomic libraries to clone 5'- and 3'insert flanking regions are shown by the SalI-SalI and NdeI-NdeI restriction sites on the map. (B) Gene structure of the tla1 mutant and wild type *C. reinhardtii* in the pJD67 plasmid insertion locus: 104 bp of 5' UTR, a total coding region of 642 bp (coding region of exon 1 with 198 bp and coding region of exon 2 with 444 bp), a single intron of 116 bases and 1.26 kb of 3' UTR, encoding a protein of 213 amino acids.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" may include both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The phrase "nucleic acid sequence encoding" refers to a nucleic acid that codes for an amino acid sequence of at least 5 contiguous amino acids within one reading frame. The amino acid need not necessarily be expressed when introduced into a cell or other expression system, but may merely be determinable based on the genetic code. For example, the sequence ATGATGGAGCATCAT (SEQ ID NO:29) encodes MMEHH. (SEQ ID NO:30). Thus, a polynucleotide may encode a polypeptide sequence that comprises a stop codon or contains a changed frame so long as at least 5 contiguous amino acids within one reading frame. The nucleic acid sequences may include both the DNA strand sequence that is transcribed into RNA and the RNA sequence. The nucleic acid sequences include both the full length nucleic acid sequences as well as fragments from the full length sequences. It should be further understood that the sequence includes the degenerate codons of the native sequence or sequences which may be introduced to provide codon preference in a specific host cell.

The term "promoter" or "regulatory element" refers to a region or sequence determinants located upstream or downstream from the start of transcription that are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

As used herein, the term "algal regulatory element" or "algae promoter" refers to a nucleotide sequence that, when operatively linked to a nucleic acid molecule, confers e expression upon the operatively linked nucleic acid molecule in unicellular green algae. It is understood that limited modifications can be made without destroying the biological function of a regulatory element and that such limited modifications can result in algal regulatory elements that have substantially equivalent or enhanced function as compared to a wild type algal regulatory element. These modifications can be deliberate, as through site-directed mutagenesis, or can be accidental such as through mutation in hosts harboring the regulatory element. All such modified nucleotide sequences are included in the definition of an algal regulatory element as long as the ability to confer expression in unicellular green algae is substantially retained.

The term "suppressed" or "decreased" encompasses the absence of Tla1 protein in a plant, e.g., algae, as well as protein expression that is present but reduced as compared to the level of Tla1 protein expression in a wild type plant, e.g., algae. The term "suppressed" also encompasses an amount of Tla1 protein that is equivalent to wild type levels, but where the protein has a reduced level of activity in comparison to wild type plants. Generally, at least a 20% decrease in Tla1 activity, amount, chlorophyll antenna size or the like is preferred, with at least about 50% or at least about 75% being particularly preferred.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A "Tla1 polynucleotide" is a nucleic acid sequence substantially similar to SEQ ID NO:1 or SEQ ID NO:3, or that encodes a polypeptide that is substantially similar to SEQ ID NO:2. Tla1 polynucleotides may comprise (or consist of) a region of about 15 to about 3,000 or more nucleotides, sometimes from about 20, or about 50, to about 2,000 nucleotides and sometimes from about 200 to about 600 nucleotides, which hybridizes to SEQ ID NO:1 or SEQ ID NO:3, or the complements thereof, under stringent conditions, or which encodes a Tla1 polypeptide or fragment of at least 15 amino acids thereof. Tla1 polynucleotides can also be identified by their ability to hybridize under low stringency conditions (e.g., Tm ~40° C.) to nucleic acid probes having the sequence of SEQ ID NO:1 or SEQ ID NO:3. Such Tla1 nucleic acid sequence can have, e.g., about 25-30% base pair mismatches or less relative to the selected nucleic acid probe. SEQ ID NOs:1 and 3 are exemplary Tla1 polynucleotide sequences. The term "Tla1 polynucleotide" encompasses antisense as well as sense nucleic acids.

A "Tla1 polypeptide" is an amino acid sequence that is substantially similar to SEQ ID NO:2, or a fragment or domain thereof. A full-length Tla1 protein is 213 amino acids. The majority of the amino acid residues are hydrophilic, suggesting that it is a soluble cytosolic protein. A single hydrophobic domain is present. The domain comprises 27 amino acids between residues 42 and 69 (with reference to SEQ ID NO:2). The hydrophobic domain is highly conserved in diverse organisms.

As used herein, a homolog or ortholog of a particular Tla1 gene (e.g., SEQ ID NO:1) is a second gene in the same plant type or in a different plant type, which has a polynucleotide sequence of at least 50 contiguous nucleotides which are substantially identical (determined as described below) to a sequence in the first gene. It is believed that, in general, homologs or orthologs share a common evolutionary past.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a Tla1 gene. In addition, the term specifically includes sequences (e.g., full length sequences) substantially identical (determined as described below) with a Tla1 gene sequence. A "polynucleotide sequence from" a Tla1 gene can encode a protein that retains the function of a Tla1 polypeptide in contributing to chlorophyll antenna size.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence. Thus, an introduced "polynucleotide sequence from" a Tla1 gene may not be identical to the target Tla1 gene to be suppressed, but is functional in that it is capable of inhibiting expression of the target Tla1 gene.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" in the context of polynucleotide sequences means that a polynucleotide comprises a sequence that has at least 50% sequence identity. Alternatively, percent identity can be any integer from 40% to 100%. Exemplary embodiments include at least: 50%, 55%, 60%, 65%, 70%, 75%, 80%, 85%, 90%, 95%, or 99%. compared to a reference sequence using the programs described herein; preferably BLAST using standard parameters, as described below. Accordingly, Tla1 sequences of the invention include nucleic acid sequences that have substantial identity to SEQ ID NO:1, or a portion of SEQ ID NO:1 such as the coding region of SEQ ID NO:1, or SEQ ID NO:3.

Tla1 polypeptide sequences of the invention include polypeptide sequences having substantial identify to SEQ ID NO:2. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 50%. Preferred percent identity of polypeptides can be any integer from 50% to 100%, e.g., at least 50%, 55%, 60%, 65%, 70%, 75%, 80%, 85%, 90%, 95%, or 99%, an sometimes at least 61%, 62%, 63%, 64%, 65%, 66%, 67%, 68%, 69%, 70%, 71%, 72%, 73%, 74% and 75%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by Tla1 genes of the invention can be identified in Northern blots under stringent conditions using cDNAs of the invention or fragments of at least about 100 nucleotides. For the purposes of this disclosure, stringent conditions for such RNA-DNA hybridizations are those which include at least one wash in 0.2× SSC at 63° C. for 20 minutes, or equivalent conditions. Genomic DNA or cDNA comprising genes of the invention can be identified using the same cDNAs (or fragments of at least about 100 nucleotides) under stringent conditions, which for purposes of this disclosure, include at least one wash (usually 2) in 0.2× SSC at a temperature of at least about 50° C., usually about 55° C., for 20 minutes, or equivalent conditions.

A Tla1 gene for use in the invention can also be amplified using PCR techniques. For example, a Tla1 gene of the invention may be amplifiable by the primer set: (5' TACGG-GAATTTGCGGAACCTC 3'; (SEQ ID NO:4) and" (5' AACACACACCCCGCACT 3'; (SEQ ID NO:7).

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

Introduction

The present invention provides methods of suppressing Tla1 gene expression in plants, e.g., green algae. Plants having suppressed Tla1 gene expression exhibit decreases in the size of chlorophyll antenna. Such plants are useful for many purposes. For example, Tla1 suppression can be used to enhance plant growth and photosynthetic productivity. In embodiments where the plant is a green algae, such Tla1-suppressed plants can be used, e.g., in mass culture for production of various nutrients or pharmaceuticals, for production of $H_2$, for production of lipid/hydrocarbons, for carbon sequestration, for waste-water treatment and aquatic pollution amelioration, for flu gas treatment and atmospheric pollution amelioration, for biomass generation, and for other purposes.

A Tla1 nucleic acid that is targeted for suppression in this invention encodes a Tla1 protein that is substantially similar to SEQ ID NO:2, or a fragment thereof. For example, such Tla1 proteins have one or more conserved domains, designated with reference to SEQ ID NO:2: amino acid positions 9-33, amino acid positions 41-70, amino acid positions 75-129, amino acid positions 135-163, or amino acid positions 177-200. Other exemplary plant Tla1-related polynucleotide sequences are from *Oryza sativa* (Accession No. CX102072), *Zea mays* (Accession No. EB673149), and *Arabidopsis thaliana* (Accession No. DR308999). Examples of conserved regions of these proteins are shown in FIG. 13. 1. Other exemplary Tla1-related sequences include those from *Solanum tuberosum* (potato) (Accession No. . . CV500710); *Gossypium arboreum* (Accession No. BG44500); *Helianthus annuus* (Accession No. BQ967999); *Nicotiana tabacum* (tobacco) (Accession No. EB678062); *Triticum aestivum* (wheat) (Accession No. CV065526); *Hordeum vulgare* (barley) (Accession No. AL504185); and *Glycine max* (soybean) (Accession No. BM107844).

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999).

TLA1 Nucleic Acid Sequences

Isolation or generation of Tla1 polynucloetide sequence can be accomplished by a number of techniques. For instance, oligonucleotide probes based on the sequences disclosed here can be used to identify the desired polynucleotide in a cDNA or genomic DNA library from a desired plant species. Such a cDNA or genomic library can then be screened using a probe based upon the sequence of a cloned Tla1 gene, e.g., SEQ ID NO:1 or 3. Probes may be used to hybridize with genomic DNA or cDNA sequences to isolate homologous genes in the same or different plant species.

Alternatively, the nucleic acids of interest can be amplified from nucleic acid samples using amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a Tla1 gene from plant cells, e.g., algae, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Exemplary primer pairs are: "primer 1" (5' TACGGGAATTTGCGGAACCTC 3'; (SEQ ID NO:4) and "primer 6" (5' AACACACACCCCG-CACT 3'; (SEQ ID NO:7) set out in Table 1 hereinbelow. Exemplary amplification reaction conditions are: 20 mM Tris HCl, pH 8.4, 50 mM potassium chloride, 2.5 mM magnesium chloride, 0.25 mM dATP, 0.25 mM dCTP, 0.25mM dGTP, 0.25 mM dTTP, 0.6 µM primers, and 2.5 units Taq polymerase/PCR reaction. An exemplary thermal cycling program is 94° C. for 3 min., 35 cycles of 95° C. for 45 sec, 55° C.-59° C. for 30 sec, 72° C. for 130 sec, followed by 72° C. for 10 min.

The genus of Tla1 nucleic acid sequences for use in the invention includes genes and gene products identified and characterized by techniques such as hybridization and/or sequence analysis using exemplary nucleic acid sequences, e.g., SEQ ID NOs:1 and 3, and protein sequences, e.g., SEQ ID NO:2.

Preparation of Recombinant Vectors

To use isolated sequences in the above techniques, recombinant DNA vectors suitable for transformation of plant cells, e.g., green algae cells, are prepared. Techniques for transforming a wide variety of higher plant species are well known and described in the technical and scientific literature. See, for example, Weising et al. *Ann. Rev. Genet.* 22:421-477 (1988). For example, a DNA sequence encoding a sequence to suppress Tla1 expression (described in further detail below), will preferably be combined with transcriptional and other regulatory sequences which will direct the transcription of the sequence from the gene in the intended cells of the transformed plant.

Regulatory sequences include promoters, which may be either constitutive or inducible, or where a higher plant is involved, tissue-specific. For example, a plant promoter fragment may be employed that is constitutive, i.e., it will direct expression of the gene under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumafaciens*, the CaMV 19S promoter; the Figwort mosaic virus promoter; actin promoters, and the nopaline synthase (nos) gene promoter. Other constitutive promoter include promoters such as the *Arabidopsis* actin gene promoter (see, e.g., Huang (1997) *Plant Mol. Biol.* 1997 33:125 139); alcohol dehydrogenase (Adh) gene promoters (see, e.g., Millar (1996) *Plant Mol. Biol.* 31:897 904); ACT11 from *Arabidopsis* (Huang et al. *Plant Mol. Biol.* 33:125-139 (1996)), Cat3 promoter from *Arabidopsis* (Zhong et al., *Mol. Gen. Genet.* 251:196-203 (1996)), the promoter from the gene encoding stearoyl-acyl carrier protein desaturase from *Brassica napus* (Solocombe et al. *Plant Physiol.* 104:1167-1176 (1994)), GPc1 promoter from maize (Martinez et al. *J. Mol. Biol.* 208:551-565 (1989)), Gpc2 promoter from maize (Manjunath et al., *Plant Mol. Biol.* 33:97-112 (1997)), and other transcription initiation regions from various plant genes known to those of skill. Chimeric regulatory elements, which combine elements from different genes, also can be useful for e expressing a nucleic acid molecule encoding a Tla polynucleotide.

Alternatively, a plant promoter can be used to direct expression of Tla1 nucleic acid under the influence of changing environmental conditions. Examples of environmental conditions that may effect transcription by inducible promoters include anaerobic conditions, elevated temperature, or the presence of light. Plant promoters that are inducible upon exposure to chemicals reagents, such as herbicides or antibiotics, are also used to express Tla1 nucleic acids. For example, the maize In2 2 promoter, activated by benzenesulfonamide herbicide safeners, can be used (De Veylder (1997) Plant Cell Physiol. 38:568 577). Other useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)), or a light.

In one example, a promoter sequence that is responsive to light may be used to drive expression of a Tla1 nucleic acid construct that is introduced into *Chlamydomonas* that is exposed to light (e.g., Hahn, *Curr Genet* 34:459-66, 1999; Loppes, *Plant Mol Biol* 45:215-27, 2001; Villand, *Biochem J* 327:51-7), 1997. Other light-inducible promoter systems may also be used, such as the phytochrome/PIF3 system (Shimizu-Sato, *Nat Biotechnol* 20): 1041-4, 2002). Further, a promoter can be used that is also responsive to heat can be employed to drive expression in algae such as *Chlamydomonas* (Muller, *Gene* 111:165-73, 1992; von Gromoff, *Mol Cell Biol* 9:3911-8, 1989). Additional promoters, e.g., for expression in algae such as green microalgae, include the RbcS2 and PsaD promoters (see, e.g., Stevens et al., *Mol. Gen. Genet.* 251:23-30, 1996; Fischer & Rochaix, *Mol Genet Genomics* 265:888-94, 2001).

In some embodiments, the promoter may be from a gene associated with photosynthesis in the species to be transformed or another species. For example such a promoter from one species may be used to direct expression of a protein in transformed algal cells or cells of another photosynthetic marine organism. Suitable promoters may be isolated from or synthesized based on known sequences from other photosynthetic organisms. Preferred promoters are those for genes from other photosynthetic species that are homologous to the photosynthetic genes of the algal host to be transformed. For example, a series of light harvesting promoters from the fucoxanthin chlorophyll binding protein have been identified in *Phaeodactylum tricornutum* (see, e.g., Apt, et al. *Mol Gen. Genet.* 252:572-579, 1996). In other embodiments, a carotenoid chlorophyll binding protein promoter, such as that of peridinin chlorophyll binding protein, can be used.

In some embodiments, promoters are identified by analyzing the 5' sequences of a genomic clone corresponding to the Tla1 genes described here. Sequences characteristic of promoter sequences can be used to identify the promoter. Sequences controlling eukaryotic gene expression have been extensively studied and include basal elements such as CG-rich regions, TATA consensus sequences etc. In plants, further upstream, there is typically a promoter element with a series of adenines surrounding the trinucleotide G (or T) N G. J. Messing et al., in GENETIC ENGINEERING IN PLANTS, pp. 221-227 (Kosage, Meredith and Hollaender, eds. (1983)).

A number of methods are known to those of skill in the art for identifying and characterizing promoter regions in plant genomic DNA (see, e.g., Jordano, et al., *Plant Cell*, 1:855 866 (1989); Bustos, et al., *Plant Cell*, 1:839 854 (1989); Green, et al., *EMBO J.* 7, 4035 4044 (1988); Meier, et al., *Plant Cell*, 3, 309 316 (1991); and Zhang, et al., *Plant Physiology* 110:1069 1079 (1996)). A promoter can be additionally evaluated by testing the ability of the promoter to drive expression in plant cells, e.g., green algae, in which it is desirable to introduce a Tla1 expression construct.

The vector comprising Tla1 nucleic acid sequences will typically comprise a marker gene that confers a selectable phenotype on plant or algae cells. Such markers are known. For example, the marker may encode biocide resistance, particularly antibiotic resistance, such as resistance to zeocin, kanamycin, G418, bleomycin, hygromycin, or herbicide resistance, such as resistance to chlorosluforon or Basta. In some embodiments, selectable markers for use in *Chlamydomonas* can be markers that provide spectinomycin resistance (Fargo, *Mol Cell Biol* 19:6980-90, 1999), kanamycin and amikacin resistance (Bateman, *Mol-Gen Genet* 263:404-10, 2000), zeomycin and phleomycin resistance (Stevens, *Mol Gen Genet* 251:23-30, 1996), and paramomycin and neomycin resistance (Sizova, *Gene* 277:221-9, 2001).

Tla1 nucleic acid sequences of the invention can be expressed recombinantly in plant cells, e.g., green algae, or other host cell expression systems, such as bacteria, yeast, and the like, to increase levels of Tla1 polypeptides. As appreciated by one of skill in the art, expression constructs can be designed taking into account such properties as codon usage frequencies of the organism in which the Tla1 nucleic acid is to be expressed. Tla1 polypeptides can be used, e.g., for the production of antibodies to monitor Tla1 expression. Alternatively, antisense or other Tla1 constructs are used to suppress Tla1 levels of expression.

A variety of different expression constructs, such as expression cassettes and vectors suitable for transformation of plant cells can be prepared. Techniques for transforming a wide variety of plant species are well known and described in the technical and scientific literature. See, e.g., Weising et al. *Ann. Rev. Genet.* 22:421-477 (1988). For example, a Tla1 nucleic acid construct can be directly introduced into a plant or algae cell by microparticle bombardment, or using a glass bead method (e.g., Kindle, *Proc. Natl. Acad. Sci. USA* 87:1228-1232, 1990). Alternatively, e.g., when transfecting higher plants, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Other techniques are also known. For example, the introduction of DNA constructs using polyethylene glycol precipitation is described in Paszkowski et al. *EMBO J.* 3:2717-2722 (1984). Electroporation techniques are described in Fromm et al., *Proc. Natl. Acad. Sci. USA* 82:5824 (1985). Ballistic transformation techniques are described in Klein et al., *Nature* 327:70-73 (1987).

In some embodiments, Tla1 nucleic acid constructs are introduced into algae, e.g., green algae. As noted above, the nuclear, mitochondrial, and chloroplast genomes can be transformed through a variety of known methods (see, e.g., Kindle, *J Cell Biol* 109:2589-601, 1989; Kindle, *Proc Natl Acad Sci USA* 87:1228-32, 1990; Kindle, *Proc Natl Acad Sci USA* 88:1721-5, 1991; Shimogawara, *Genetics* 148:1821-8, 1998; Boynton, *Science* 240:1534-8, 1988; Boynton, *Methods Enzymol* 264:279-96, 1996; Randolph-Anderson, *Mol Gen Genet* 236:235-44, 1993).

Suppression of Tla1 Expression

The invention provides methods for generating a plant having a reduced chlorophyll antenna size by suppressing expression of a nucleic acid molecule encoding Tla1. In a transgenic plant of the invention, a nucleic acid molecule, or antisense constructs thereof, encoding a Tla1 gene product can be operatively linked to an exogenous regulatory element. The invention provides, for example, a transgenic plant characterized by reduced chlorophyll antenna size having an expressed nucleic acid molecule encoding a Tla1 gene product, or antisense construct thereof, that is operatively linked to an exogenous constitutive regulatory element. In one embodiment, the invention provides a transgenic plant that is characterized by small chlorophyll antenna size due to suppression of a nucleic acid molecule encoding a Tla1 polypeptide. Such a plant typically comprises an expression cassette stably transfected into the plant cell, such that that Tla1 polypeptide expression is inhibited constitutively or under certain conditions, e.g., when an inducible promoter is used.

Tla1 nucleic acid sequences can be used to prepare expression cassettes useful for inhibiting or suppressing Tla1 expression. A number of methods can be used to inhibit gene expression in plants. For instance, siRNA, antisense, or ribozyme technology can be conveniently used. For example, in *Chlamydomonas*, antisense inhibition can be used to decrease expression of a targeted gene (e.g., Schroda, *Plant Cell* 11:1165-78, 1999). Alternatively, an RNA interference construct can be used (e.g., Schroda, *Curr Genet.* 49:69-84, 2006, Epub 2005 Nov. 25).

For antisense expression, a nucleic acid segment from the desired Tla1 gene is cloned and operably linked to a promoter such that the antisense strand of RNA will be transcribed. The expression cassette is then transformed into plants, e.g., algae, and the antisense strand of RNA is produced. The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of Tla1 can be useful for producing a plant in which Tla1 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. SEquences can also be longer, e.g., 1000 or 2000 nucleotides are greater in length.

Catalytic RNA molecules or ribozymes can also be used to inhibit expression of Tla1 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs.

A number of classes of ribozymes have been identified. One class of ribozymes is derived from a number of small circular RNAs that are capable of self-cleavage and replication in plants. Ribozymes, e.g., Group I introns, have also been identified in the chloroplast of green algae (see, e.g., Cech, *Annu Rev Biochem* 59:543-568, 1990; Bhattacharya, *Molec Biol and Evol* 13:978-989, 1996; Erin, et al., *Amer J Botany* 90:628-633, 2003; Turmel, et al., *Nucl Acids Res.* 21:5242-5250, 1993; and Van Oppen et al., *Molec Biol and Evol* 10:1317-1326, 1993). The design and use of target RNA-specific ribozymes is described, e.g., in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 90% or 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by means of RNA interference (RNAi), which uses a double-stranded RNA having a sequence identical or similar to the sequence of the target TLA1 gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementry RNAs or may be a single RNA with internally complementary sequences that form a double-stranded RNA. The introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97:4985 (2000); Waterhouse et al., *Proc. Natl. Acad. Sci. USA* 95:13959-13964 (1998); Tabara et al. *Science* 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest, e.g., green algae. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 15, 20, 25, 30, 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Thus, RNAi fragments may be selected for similarity or identity with the N terminal region of the Tla1 sequences of the invention (i.e., those sequences lacking significant homology to sequences in the databases) or may be selected for identity or similarity to conserved regions of Tla1 proteins, e.g., the hydrophobic region.

Expression vectors that continually express siRNA in transiently- and stably-transfected cells have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2:110-119 (2001), Fire et al. *Nature* 391:806-811 (1998) and Timmons and Fire *Nature* 395:854 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variation between family members.

Screening for Plants Having Suppressed Tla1 Expression

The invention also provides methods of screening for plants, e.g., green algae, having reduced Tla1 gene expression. Such plants can be generated using the techniques described above to target Tla1 genes. In other embodiments mutagenized plants, e.g., algae, can be screened for reduced Tla1 gene expression.

Methods for introducing genetic mutations into plant genes and selecting plants with desired traits are well known. For instance, plant cells can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used. In other embodiments, insertional mutagenesis can be performed (see, e.g., Polle et al., *Planta* 217:49-59, 2003).

Alternatively, homologous recombination can be used to induce targeted gene modifications by specifically targeting a Tla1 gene in vivo to suppress expression (see, generally, Grewal and Klar, *Genetics* 146:1221-1238 (1997) and Xu et al., *Genes Dev.* 10:2411-2422 (1996)). Homologous recombination has been demonstrated in plants (Puchta et al., *Experientia* 50:277-284 (1994), Swoboda et al., *EMBO J.* 13:484-489 (1994); Offringa et al., *Proc. Natl. Acad. Sci. USA* 90:7346-7350 (1993); and Kempin et al. *Nature* 389:802-803 (1997)).

In applying homologous recombination technology to the genes of the invention, mutations in selected portions of Tla1 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91:4303-4307 (1994); and Vaulont et al., *Transgenic Res.* 4:247-255 (1995) are conveniently used to increase the efficiency of selecting for decreased Tla1 gene expression in transgenic plants. The mutated gene will interact with the target wild-type gene in such a way that homologous recombination and targeted replacement of the wild-type gene will occur in transgenic plant cells, resulting in suppression of Tla1 activity.

Alternatively, oligonucleotides composed of a contiguous stretch of RNA and DNA residues in a duplex conformation with double hairpin caps on the ends can be used. The RNA/DNA sequence is designed to align with the sequence of the target Tla1 gene and to contain the desired nucleotide change. Introduction of the chimeric oligonucleotide on an extrachromosomal T-DNA plasmid results in efficient and specific Tla1 gene conversion directed by chimeric molecules in a small number of transformed plant cells. This method is described in Cole-Strauss et al., *Science* 273:1386-1389 (1996) and Yoon et al., *Proc. Natl. Acad. Sci. USA* 93:2071-2076 (1996).

In other embodiments, insertional mutagenesis can be used to mutagenize a population of plants, e.g., green algae, that can subsequently be screened.

Plants, e.g., green algae, with mutations can be screened for decreased Tla1 gene expression. Such decreases are determined by examining levels of Tla1 gene or protein expression. Techniques for performing such an analysis are readily known in the art and include quantitative RT-PCR, northern blots, immunoassays, and the like. Tla1 expression can also be evaluated by analyzing a phenotypic endpoint such as chlorophyll antenna size and selecting plants having reduce chlorophyll antenna size relative to normal.

Plants that can be Targeted

Tla1 can be suppressed in any number of eukaryotic green plants where it is desirable to reduce the rate of light absorption. For example, crop plants, such as tobacco, soybeans, barley, maize, and others (see, e.g., Okabe, et al., *J Plant Physiol.* 60:150-156, 1977; Melis & Thielen, *Biochim. Biophys. Acta* 589:275-286, 1980; Ghirardi et al., *Biochim. Biophys. Acta* 851:331-339, 1986; Ghirardi & Melis, *Biochim. Biophys. Acta* 932:130-137, 1988; Droppa, et al., *Biochim. Biophys. Acta* 932:138-145, 1988; and Greene, et al., *Plant Physiol.* 87:365-370, 1988).

Uses of Tla1 Suppressed Algae

In some embodiments, Tla1 is suppressed in algae. Algae, alga or the like, refer to plants belonging to the subphylum Algae of the phylum Thallophyta. The algae are unicellular, photosynthetic, anoxygenic algae and are non-parasitic plants without roots, stems or leaves; they contain chlorophyll and have a great variety in size, from microscopic to large seaweeds. Green algae, which are single cell eukaryotic organisms of oxygenic photosynthesis endowed with chlorophyll a and chlorophyll b belonging to Eukaryota—Viridiplantae—Chlorophyta—Chlorophyceae, are often a preferred target. For example, Tla1 expression can be suppressed in *C. reinhardtii*, which is classified as Volvocales—Chlamydomonadaceae. Algae strains that are of particular interest for this invention are, e.g., *Chlamydomonas reinhardtii, Scenedesmus obliquus, Chlorella vulgaris, Botryococcus braunii, Botryococcus sudeticus, Dunaliella salina*, and *Haematococcus pluvialis*.

Algae can be used in high density photobioreactors (see, e.g., Lee et al., *Biotech. Bioengineering* 44:1161-1167, 1994; Chaumont, *J Appl. Phycology* 5:593-604, 1990), bioreactors for sewage and waste water treatments (e.g., Sawayama et al., *Appl. Micro. Biotech.,* 41:729-731, 1994; Lincoln, *Bulletin De L'institut Oceangraphique (Monaco)*, 12:109-115, 1993), elimination of heavy metals from contaminated water (e.g., Wilkinson, *Biotech. Letters,* 11:861-864, 1989), the production of β-carotene (e.g., Yamaoka, *Seibutsu*-Kogaku Kaishi, 72:111-114, 1994), the production of hydrogen (e.g., U.S. Patent Application Publication No. 20030162273), and pharmaceutical compounds (e.g., Cannell, 1990), as well as nutritional supplements for both humans and animals (Becker, 1993, "Bulletin De L'institut Oceanographique (Monaco), 12, 141-155) and for the production of other compounds of nutritional value.

Conditions for growing Tla1-suppressed algae for the exemplary purposes illustrated above are known in the art (see, e.g., the exemplary references cited herein).

EXAMPLES

Methodology

Growth of the Algae

*Chlamydomonas reinhardtii* strain cw15, the arginine-requiring CC425, the chlorophyll-deficient mutant tla1 and Tla1-complemented strains of the tla1 mutant were grown to the mid-exponential growth phase either in TAP [Tris Acetate Phosphate, pH 7.4], TAP+Arg (Sueoka, *Proc. Natl. Acad. Sci. USA* 46:83-91, 1960; Harris, *The Chlamydomonas source book: A comprehensive guide to biology and laboratory use*: Academic Press, San Diego, 1989), or in modified minimal media containing 40 mM Tris-HCl, pH 7.4, supplemented with 25 mM sodium bicarbonate with or without Arg (TBP medium, Polle et al., *Planta* 211:335-344, 2000) in flat 1-1 Roux bottles at 25° C. under continuous illumination of 200 µmol photons m-2 s-1 provided by cool-white fluorescent lamps. The cultures were stirred continuously to ensure a uniform illumination of the cells and to prevent settling.

Cell Count and Chlorophyll Determinations

Cell density was estimated upon counting the number of cells per ml culture using a Neubauer ultraplane hemacytometer. Pigments from intact cells were extracted in 80% acetone and cell debris removed by centrifugation at 10,000 g for 5 min. The absorbance of the supernatant was measured with a Shimadzu UV-160U spectrophotometer and the chlorophyll (a and b) concentration of the samples was determined according to Arnon, *Plant Physiol* 24:1-15, 1949, with equations corrected as in Melis et al. (*Photochem. Photobiol.* 45:129-136, 1987).

Nucleic Acid Extractions

Genomic DNA was isolated using either Stratagene's (La Jolla, Calif.) DNA purification kit or a combination of QIAGEN's (Valencia, Calif.) DNeasy plant mini kit and phenol chloroform extraction (Davies et al. 1992). BAC DNA was isolated using QIAGEN's midi prep kit. Total RNA was isolated using either QIAGENS's Plant RNeasy Kit or the Trizol Reagent (Invitrogen, Carlsbad, Calif.).

Cloning of Plasmid Insert Flanking Sequences from the tla1 Mutant

Genomic DNA of the tla1 mutant was digested with Apa I (New England Biolab, Beverly, Mass.) and size-fractionated by 0.8% agarose gel electrophoresis. Restriction enzyme digestion yielded a DNA fragment of about 5 kb, containing about 2 kb of *Chlamydomonas* genomic DNA flanking the insertion and about 3 kb portion of the 5' end of the pJD67 plasmid sequence (Polle et al. 2003, supra). Similarly, a 3.2 kb DNA fragment was identified, which contained about 2.2 kb of the 3' end of the pJD67 plasmid sequences and about 1 kb of *Chlamydomonas* genomic DNA flanking the insertion (Polle et al. 2003, supra). Therefore, following agarose gel electrophoresis of Apa I-digested tla1 genomic DNA, fragments migrating in the 6-4 kb region were used for the construction of a 5' insert flanking DNA library. Similarly, fragments migrating in the 4-3 kb region were used to construct a 3' insert flanking DNA library.

The vector was digested with Apa I and treated with alkaline phosphatase (Promega, San Luis Obispo, Calif.) to avoid self-ligation of the plasmid. DNA fragments that migrated between the molecular weight markers of 4-6 kb and 3-4 kb were gel purified using QIAEX II gel extraction kit (QIAGEN, Valencia, Calif.) and were ligated into the pZero Kan+ vector (which includes a kanamycin resistance gene, Promega, San Luis Obispo, Calif.) for the construction of a partial genomic library containing insert-5' and 3' flanking sequences. Use of the Apa I restriction enzyme in the digestion of the tla1 genomic DNA proved useful not only in the spatial separation of the 5'-insert flanking sequences from the 3'-insert flanking sequences, but also in the separation of the insert flanking sequences from the endogenous copy of the ARG7.8 gene.

About 5000 *E. coli* colonies containing the partial genomic DNA libraries of the tla1 mutant were screened using appropriate DNA probes derived from the ARG7.8 gene (Polle et al. 2003, supra). The probe Sal I-Sal I (1.3 kb representing the 5' end of the ARG7 structural gene) was used to screen a partial genomic library containing the 5'-insert flanking sequences. The probe Nde I-Nde I (0.75 kb) derived from the 3' end of the ARG7 was used to screen a partial genomic library containing the 3'-insert flanking sequences (FIG. 1).

Isolation of a BAC Clone

A DNA fragment containing the insert-3' flanking sequence was subsequently used for screening a commercially available wild type *Chlamydomonas reinhardtii* BAC library, constructed in pBACmn vector and printed on nylon membrane referred to as a high-density filter (Incyte Genomics Inc, Palo Alto, Calif.).

Southern Blotting and RACE Analysis

For Southern blot analysis, 10 μg of genomic or BAC DNA was used for restriction digestion, separated on 0.8% agarose gels for Southern blot analyses. After separation of the DNA fragments, nucleic acids were either blotted onto a positively charged nylon membrane (NEN Life Science Products, Inc, Wellesley, Mass.) or DNA was purified from excised gel pieces in the region of appropriate molecular weight. The blotted membranes were hybridized with $^{32}$P-labeled probes (Random oligonucleotides DNA Labeling System, Roche Diagnostic Corporation, Alameda, Calif.). The probe DNA was PCR-amplified using specific primers designed from the insert-3' flanking sequence of the tla1 mutant. Both of these primers were derived from the coding region of the Tla1 gene.

Tla1-cDNAs were synthesized using 1 μg of total RNA isolated from either WT or tla1 mutant with "primer 5" (Table 1) designed from the coding-2 region of the Tla1 gene and an oligo dT anchor primer (Invitrogen, Carlsbad, Calif.). These cDNAs were used as templates for 5' and 3' RACE analyses using a kit from Boehringer, Mannheim (Germany).

TABLE 1

Exemplary PCR primers and expected product sizes in wild type, tla1 mutant and tla1 complemented strains.

| Primers | Expected products from strains | | |
|---|---|---|---|
| | WT | tla1 mutant | tla1-complements |
| "primer 1" (5'TACGGGAATTTGCGGAACCTC 3'; (SEQ ID NO: 4) and | 589 bp genomic DNA product | No product | 589 bp genomic DNA product |
| "primer 4" (5'TTGTTGTCCAGCACCAGCAC 3'); (SEQ ID NO: 5) probing for the 5'UTR of Tla1 | | | |
| "primer 7" (5'CAACGCATATAGCGCTAGCAG 3'; (SEQ ID NO: 4) and | No C product | 681 bp genomic DNA product | 681 bp genomic DNA product |
| "primer 4" (5'TTGTTGTCCAGCACCAGCAC 3'; (SEQ ID NO: 7) probing for the 3'end of pJD67 | | | |

TABLE 1-continued

Exemplary PCR primers and expected product sizes in wild type, tla1 mutant and tla1 complemented strains.

| Primers | Expected products from strains | | |
|---|---|---|---|
| | WT | tla1 mutant | tla1-complements |
| "primer 1" (5'TACGGGAATTTGCGGAACCTC 3') and | 939 bp genomic DNA product; | No product | 939 bp genomic DNA product; |
| "primer 6" (5'AACACACACCCCGCACT 3'); probing for the full length Tla1 gene and transcript | 823 bp cDNA product | 823 bp cDNA product | |
| "primer 8" (5'GGGACTTCGTGGAGGACG 3'); SEQ ID NO: 8) and | No product | No product | 436 bp genomic DNA product |
| "primer 9" (5'GGTTAGTCCTGCTCCTCGG 3'; SEQ ID NO: 9) probing for the Ble gene | | | |
| "primer 3" (5' GGGCCCTTCAGCTGCTCCGCTGACC AAACC 3'; SEQ ID NO: 10) and | 409 bp cDNA product | 40 bp cDNA product | 409 bp cDNA product |
| "primer 5" (5'GGGCCCGAACGGG TTGTCCGCCTGCGCCTTGC 3'; SEQ ID NO: 11) Probing for the Tla1 transcript | | | |
| "primer 2" (5'GCTGCTCCGCTGACCAAA 3'; SEQ ID NO: 12) and | 525 bp genomic DNA product; | 525 bp genomic DNA product; | 525 bp genomic DNA product; |
| "primer 5" (5' GGGCCCGAACGGGTTGTCCGCCTG CGCCTTGC 3'; SEQ ID NO: 11 probing for the Tla1 transcript | 454 bp cDNA product | no cDNA product | 454 bp cDNA product |
| TCF (5'CGGGGTACCACTTTCAGCTGCTCCGCT 3'; SEQ ID NO: 13) and TCR (5' CCAAGCTTCCTCTT TCCCCCCCACC 3'; SEQ ID NO: 14); cloning primers used for amplifying the cDNA coding for the full length Tla1, off the cDNA library for Tla1 over-expression. PCR product size is 750 bp. | | | |

Transformation of the tla1 Mutant

BAC clone 39e16 DNA was digested with restriction enzymes ApaI or PstI. An approximately 3.7 kb DNA fragment, derived upon Apa I digestion (Apa I-Apa I), and an about 3 kb DNA fragment, derived upon Pst I digestion (Pst I-Pst I) were subcloned. The 2 kb DNA overlap region between these two clones (p5'TlaApa-4 and p3'TlaPst-3-3) was removed upon Apa I digestion of the 3 kb p3'TlaPst-3-3 clone. Subsequently, the Apa I-Apa I fragment and the 3' end of the Pst I-Pst I DNA fragment, which resulted from the ApaI digestion, were re-ligated to yield the complete 4.7 kb sequence of the Tla1 gene in pBluescript. The resulting pFTla-5 plasmid DNA was sequenced to confirm the correct coding sequence of the Tla1 gene.

The ble gene encoding zeocin resistance along with its RbcS2 promoter and terminator was excised from plasmid pSP124S (Stevens et al., *Mol. Gen. Genet.* 251:23-30, 1996) by Hind III digestion and inserted at the 5' end of the Tla1 gene in tandem to generate plasmid pSK9.2BleFTla. This plasmid was linearized upon digestion with Kpn I and used to transform the tla1 mutant by the glass bead method (Debuchy et al., *EMBO J.* 8:2803-2809, 1989). Transformant colonies were selected for zeocin resistance on TAP agar plates in the presence of 5 µM zeocin. Zeocin-resistant colonies were further screened for tla1 complementation by visual inspection of the colony coloration. Zeocin-resistant colonies having dark green coloration were tested for the presence of the wild type Tla1 gene and Tla1 protein amount by PCR/RT-PCR and Western blot analysis, respectively.

PCR and RT-PCR Analysis

Strains with tla1 mutations complemented with the Tla1 gene (tla1-complements) were first tested by PCR to check for the presence of two distinct Tla1 genes (wild type and mutant) and of the Ble tag. PCR was applied to genomic DNA by using two different forward primers, namely a Tla1 5' UTR specific primer ("primer 1": 5' TACGGGAATTTGCG-GAACCTC 3' (SEQ ID NO:4), Table 1) and a primer designed from the 3' end of the pJD67 vector that was inserted just upstream of the start codon of the Tla1 gene ("primer 7": 5' CAACGCATATAGCGCTAGCAGC 3'(SEQ ID NO:6), Table 1). A reverse primer was defined from the second exon of the Tla1 gene ("primer 4": 5' TTGTTGTCCAGCACCAG-CAC 3'(SEQ ID NO:5), Table 1). Upstream 5' UTR specific primer "primer 1" and the down stream 3' UTR specific PCR primer ("primer 6": 5' AACACACACCCCGGCACT 3'(SEQ ID NO:31), Table 1) were used to probe for the full-length Tla1 transcript. Tla1 5'UTR specific "primer 2" (5' GCT-GCTCCGCTGACCAAA 3'; SEQ ID NO:12) or Tla1 exon 1-specific "primer 3" (5' GGGCCCTTCAGCTGCTCCGCT-GACCAAACC 3'(SEQ ID NO:10), Table 1) were used in conjunction with the reverse "primer 5" (5' GGGC-CCGAACGGGTTGTCCGCCTGCGCCTTGC 3'; SEQ ID NO:11) defined from the second exon of the Tla1 gene to check for the presence of the Tla1 transcript in the tla1-complemented strains. Presence of the Ble tag was tested by PCR using a forward primer located in the second exon of the Ble gene ("primer 8": GGGACTTCGTGGAGGACG 3'SEQ ID NO:8), Table 1) and a reverse primer located in the third exon of the Ble gene ("primer 9": 5' GGTTAGTCCTGCTC-CTCGG 3' (SEQ ID NO:9), Table 1). The one-step RT-PCR kit (QIAGEN, Valencia, Calif.) was used for RT-PCR experiments. Platinum Taq polymerase (Invitrogen, Carlsbad, Calif.) was used for the PCR amplification. A 1 kb plus DNA ladder was used as DNA size markers (Invitrogen, Carlsbad, Calif.).

Generation of Tla1 Protein Overexpression Constructs

An amplified *Chlamydomonas* cDNA core library obtained from the laboratory of Dr. James V. Moroney (Louisiana State University, Baton Rouge, La.) was used to amplify Tla1 cDNA for generating the Tla1 protein overexpression construct. This cDNA library has been generated by cloning the cDNA core library (*Chlamydomonas* Genetics Center, Duke University) into the lambda ZapII vector (Stratagene, La Jolla, Calif.). In vivo excision of the pBluescript phagemid from the lambda ZapII vector, involving the Ex-Assist interference-resistant helper phage along with the SOLR strain of *E. coli* was used in the amplification of the cDNA core library.

The Tla1 cDNA sequence coding for the full length Tla1 protein was amplified from the cDNA library by PCR. The 5' end PCR primer (TCF) has the sequence 5'-CGGGGTAC-CACTTTCAGCTGCTCCGCT-3' (SEQ ID NO:13)(Table 1) and a KpnI site was incorporated at the 5' end. The 3' end PCR primer (TCR) has the sequence 5'-CCCAAGCTTC-CTCTTTCCCCCCCACC-3' (SEQ ID NO:32) and a HindIII site was incorporated at the 5' end. Amplified Tla1 cDNAs were purified from the DNA gel using the QIAEX II gel extraction kit (QIAGEN, Valencia, Calif.) and were cloned into the pQE80L overexpression vector (QIAGEN, Valencia, Calif.) which has a 6* His (SEQ ID NO:33) tag. The vector and the purified Tla1 cDNAs were double digested with Kpn I and Hind III. Ligation of the 733 bp Tla1 PCR product immediately downstream of the 6* His (SEQ ID NO:33) tag sequence in the pQE80L vector was performed following the protocol given in the New England Biolab (NEB, Beverly, Mass.) technical manual. *E. coli* strain DH5α cells were transformed. Transformants were isolated by screening colonies on LB+Amp (100 µg/mL-1) plates. In-frame insertion of Tla1 with the His tag sequence in the recombinant clone was verified by double restriction enzyme digestion analyses with Kpn I and Hind III and DNA sequencing.

Overexpression and Purification of His-tagged Tla1 Protein for the Generation of Polyclonal Specific Antibodies Selected *E. coli* clones of Tla1 were grown at 37° C. in 200 mL of LB media on a rotary shaker. The cells were induced for 5 h with 1 mM IPTG when the culture OD600 was between 0.6 and 0.7. Both induced and uninduced *E. coli* cells were harvested and resuspended in lysis buffer [100 mM $NaH_2PO_4$, 10 mM Tris-Cl (pH 8), 8 M urea] followed by sonication. Equal amounts of protein samples from induced and uninduced cells were subjected to 12.5% SDS-PAGE gel electrophoresis to test for the overexpression of the recombinant protein.

The recombinant fusion protein was purified by a one-step affinity chromatography using Ni-NTA superflow columns. Crude sonicated cell extracts were passed through Ni-NTA superflow columns (1 mL of the nickel-charged resin binds 10-15 mg of the recombinant protein). The column was washed with 6 L of wash buffer [100 mM $NaH_2PO_4$, 10 mM Tris-HCl (pH 6.3), 8 M urea]. At the final step, fusion proteins were eluted from the column by elution buffer [100 mM $NaH_2PO_4$, 10 mM Tris-HCl (pH 4.5), 8 M urea]. Purified recombinant proteins were further concentrated by a passage through Centricon columns (Amicon, Billerica, Mass.). The recombinant proteins were recovered from the membrane of the filter upon elution with phosphate buffered saline (pH 7.4) containing 137 mM NaCl, 2.7 mM KCl, 4.3 mM $NaH_2PO_4$ and 1.4 mM $KH_2PO_4$4. Purification of the recombinant protein was tested upon SDS-PAGE using the Benchmark prestained protein ladder (Invitrogen, Carlsbad, Calif. The purified recombinant protein was used for the generation of specific polyclonal antibodies (ProSci Incorporated (Poway, Calif.) following a standard protocol. Approximately 1.6 mg of protein in each of two rabbits was used to generate the Tla1 antibodies.

Cellular Protein Analysis

*Chlamydomonas* cells were harvested, washed twice with fresh medium and resuspended in TEN buffer (10 mM Tris-HCl, 10 mM EDTA and 150 mM NaCl; pH 8). Following sonication, the crude cell extract was incubated in the presence of solubilization buffer (Smith et al. 1990). Protein concentration was determined and gel lanes were loaded with an equal amount of Chl, in the range of 4 to 6 nmol Chl, as indicated. SDS-PAGE analysis was performed on a 12.5% gel, using either the Benchmark prestained or unstained protein ladder (Invitrogen, Carlsbad, Calif.), at a constant current of 10 mA for 5 h. Gels were stained with 1% Coomassie brilliant Blue R for protein visualization.

Western Blot Analysis

Electrophoretic transfer of the SDS-PAGE resolved proteins onto nitrocellulose was carried out for 2 h at a constant current of 400 mA in the transfer buffer (25 mM Tris, 192 mM glycine and 20% methanol). The titer of the Tla1 immune serum was probed with different amounts of the purified recombinant His tagged Tla1 protein (2 pg-20 ng), as well as with the total protein extract of wild type (CC425), tla1 mutant, and tla1-complements. The Tla1 immune serum was diluted with buffer [Tris-buffered saline, 0.005% Tween 20 and 1% bovine serum albumin (pH 7.4)] to a ratio of 1:3,000 before being used as a primary probe. The secondary antibody used for Western blotting was conjugated to horseradish peroxidase (BioRad, Hercules, Calif.) and diluted to a ratio of 1:30,000 with the antibody buffer. Western blots were developed by using The Supersignal West chemiluminescent substrate kit (Pierce, Rockford, Ill.).

Accession Numbers

GenBank Accession numbers for the exemplary Tla1 sequences in the examples are AF534570 (complete Tla1 genomic DNA sequence with exons and intron) and AF534571 (complete mRNA sequence with 5' and 3' untranslated regions).

Example 1

Cloning of the Tla1 Gene

Southern blot analyses of the *Chlamydomonas reinhardtii* tla1 mutant revealed a single pJD67 plasmid insert in the nuclear genome. Genetic crosses and random progeny analyses revealed that the exogenous ARG7.8 gene co-segregated with the tla1 phenotype (Polle et al. 2003, supra). On the basis of these properties, it was inferred that insertion of the pJD67 plasmid must have interrupted, or deleted, a gene that is involved in the regulation of the light-harvesting Chl antenna size of photosynthesis.

The 5' end vector sequence information, required for plasmid rescue, had been deleted from the insert site (FIG. 1A). Thus, plasmid rescue could not be employed for the cloning of the genomic DNA that is flanking the insert. To identify the gene, two different partial genomic libraries of the tla1 mutant, representing the 5' and 3' plasmid insert flanking sequences were constructed and screened with appropriate probes (see Materials and methods). Three positive clones were identified from the 5' insert flanking DNA library and only one positive clone from the 3' insert flanking DNA library. All of the above four positive clones were confirmed by restriction enzyme and sequence analysis.

A database search with the 5'-insert flanking sequence did not show significant homology to any existing EST sequences. However, a BLAST search with the 3'-insert flanking sequence matched the *Chlamydomonas* EST sequence 894001DO4.y1, which was deposited in the GenBank with Accession No. BE024188. The designation 'y' in this EST sequence denoted a 5' end of the respective cDNA.

Isolation of a BAC Clone Containing the Full Length Tla1 Gene

The 3'-insert flanking sequence of tla1 was used to screen a high-density filter containing a *Chlamydomonas* wild type BAC library. A BAC clone, number 39e16, was identified as containing the complete Tla1 gene sequence. Southern blot analysis of the 39e16 clone DNA with several restriction enzymes (using the 3'-insert flanking sequence as a probe) permitted construction of a Tla1 restriction map.

FIG. 1A shows a map of the pJD67 insertion site in the nuclear genome of the tla1 mutant. It is shown that about 2.3 kb of the 5' end of the pJD67 was deleted upon plasmid insertion in the *C. reinhardtii* nuclear genome. It is also shown that about 6 kb of genomic DNA was deleted upon plasmid insertion. Nine bps of the 3' end of the plasmid sequences were also deleted upon plasmid insertion.

A full-length cDNA was obtained upon RT-PCR, and 5' and 3' RACE analyses using cDNA from the WT (cw15) strain. The full-length cDNA showed an open reading frame encoding a protein of 213 amino acids. DNA sequence analyses of the 39e16 BAC clone revealed the structure of the full-length Tla1 genomic DNA. Genomic and cDNA analysis of the Tla1 gene showed the presence of a 104 bp 5' UTR, a single intron of 116 bases, and 1.26 kb of 3' UTR. FIG. 1B also compares the DNA structure in the Tla1 upstream region in wild type and tla1 mutant. In the tla1 mutant, the 3' end of the pJD67 plasmid replaced the promoter and 5' UTR of the wild type gene.

Figure 2:
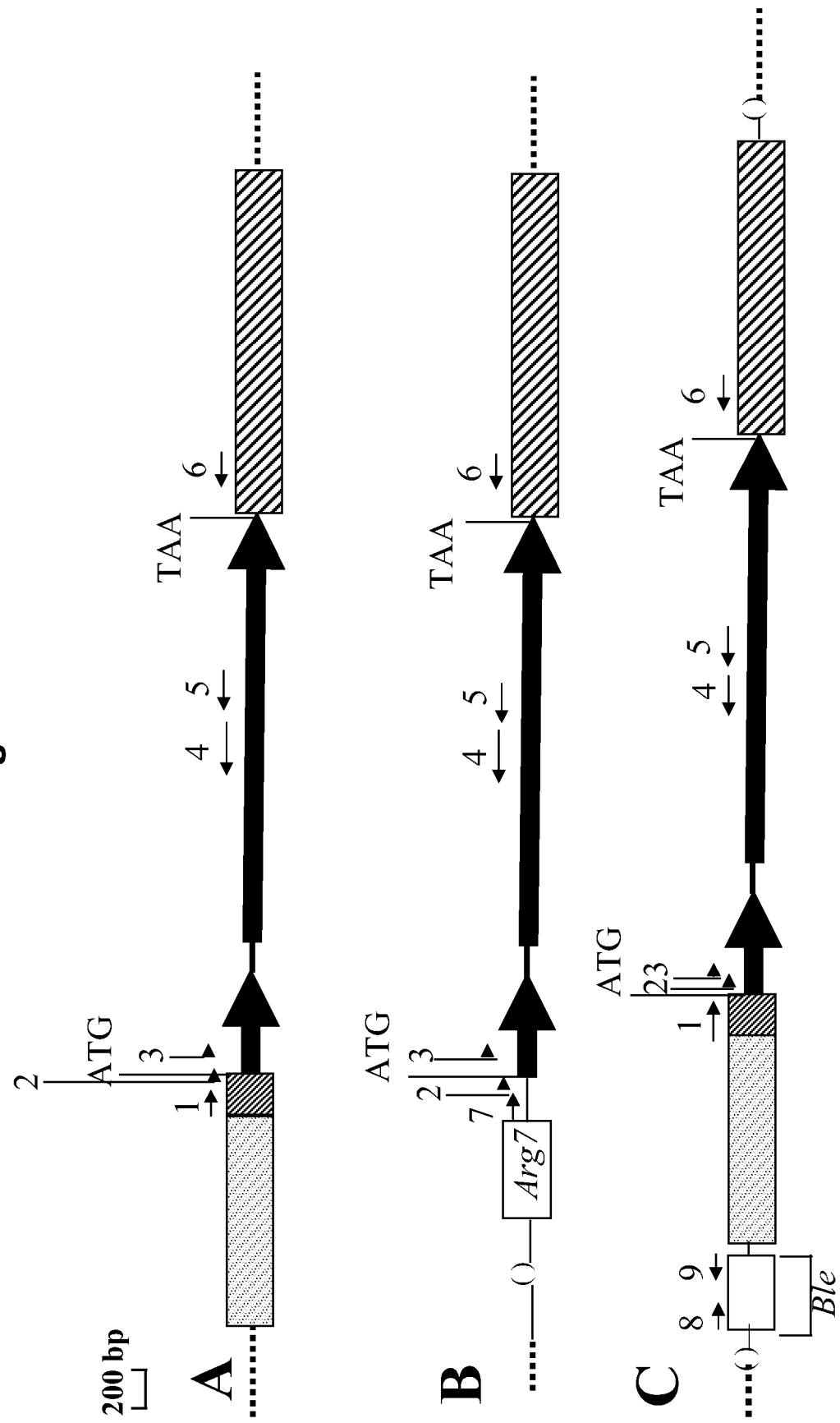
FIG. 2. Genomic DNA map showing the Tla1 gene structure in: (A) the host CC425 strain, (B) the tla1 mutant, and (C) the Tla1 complementing plasmid containing the ble gene. Note that the tla1-complements will have both the mutant gene shown in (B) and the wild type gene shown in (C). Dotted rectangles denote the promoter region of the Tla1 gene; Small hatched rectangles denote the 5' UTR of the Tla1 gene; Long-hatched rectangles denote the 3' UTR of the Tla1 gene. Thick black arrows and black lines denote the Tla1 exons and introns, respectively. Primers 1, 2, 3, 4, 5, 6, 7, 8 and 9 were used for PCR analysis and are denoted by small black arrows on the genomic DNA map (see Table 1).
Figure 3:
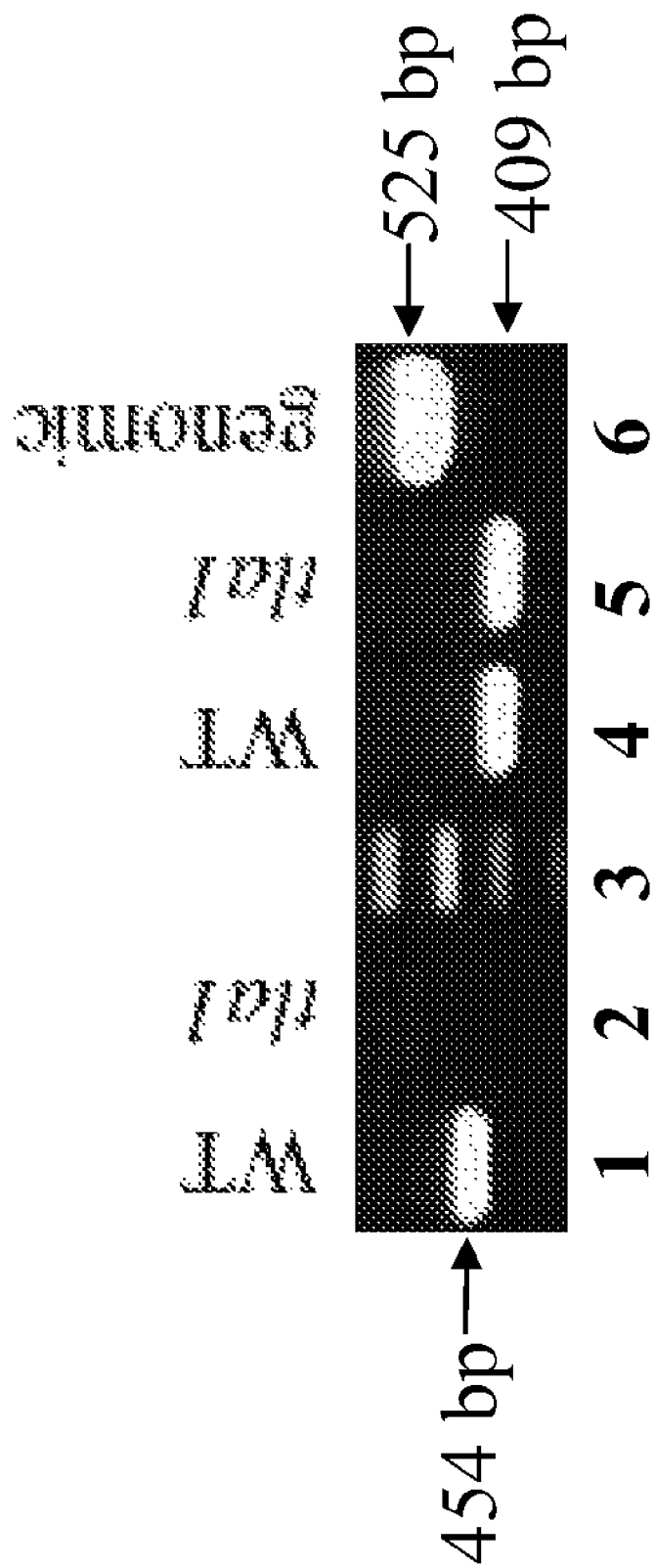
FIG. 3. PCR analysis of wild type and tla1 mutant. The presence of transcripts of the Tla1 gene was tested by RT-PCR with primers from different regions of the Tla1 cDNA. Total RNA was isolated from TBP-grown *Chlamydomonas reinhardtii* wild type and tla1 mutant cultures. The down stream PCR primer, "primer 5" was designed from the exon 2 region of the Tla1 gene and were the same for all lanes in this experiment. Lanes 1, 2: upstream primer "primer 2" was designed from the 5' UTR region ("primer 2"-GCCTGCCA-CAACCTCAGACCAAGAGACG; SEQ ID NO:15); expected product size of 454 bp). Lanes 4-6: upstream primers were designed from the exon 1 region of the Tla1 gene ("primer 3"-GGGCCCTTCAGCTGCTCCGCTGAC-CAAACC); SEQ ID NO:10). Lanes 4, 5: expected product size of 409 bp., Lane 6: genomic DNA was isolated from the tla1 mutant and used as a template for the PCR reaction; expected product size of 525 bp, i.e., larger than those of lanes 4, 5, due to the presence of a 116 bp intron, existing between exons 1 and 2. The 1.5% agarose gel was also loaded with M markers (Lane 3) containing a 1 kb DNA ladder (Promega, Madison, Wis.). The PCR products in lane 4 and 5 aligned at the 396 bp marker. The PCR products in lane 6 aligned at a position slightly higher than the 506-517 bp markers.

Transcription of the Tla1 gene in wild type and tla1 mutant was tested by RT-PCR and compared to that of genomic DNA PCR. Given the presence of the pJD67 insert in the 5' UTR of the Tla1 gene, a question was raised as to whether the tla1 mutant was able to transcribe the remnant of the Tla1 gene. RT-PCR was performed with a forward primer designed from the 5' UTR sequence of Tla1, ("primer 2") and a reverse primer ("primer 5") from the coding-2 sequence of this gene (FIG. 2). This RT-PCR yielded products in the WT but not in the tla1 mutant (FIG. 3, lanes 1 and 2). With the set of PCR primers that were designed from within the coding sequence of the Tla1 ("primer 3" and "primer 5"), RT-PCR yielded products in both the WT and tla1 mutant (FIG. 3, lanes 4 and 5). PCR products obtained with the same primers from the genomic DNA of the tla1 strain were 116 bp larger than those obtained from the cDNA due to the presence of an intron (FIG. 3, lane 6).

5' Race analysis of the Tla1 cDNAs from the wild type and mutant revealed polymorphism in the 5' UTR sequences of wild type and tla1 mutant. FIG. 4 (upper) shows the 5' RACE analysis of the wild type cDNA with a portion of the 5' UTR, the ATG start codon, and the corresponding downstream coding nucleotide sequence. In the tla1 mutant (FIG. 4, middle panel), the ATG start codon is preserved. However, the entire upstream 5' UTR and promoter regions of the Tla1 gene are deleted and replaced by the 3' end of the pJD67 plasmid sequence, represented by the lower case and underlined nucleotide sequence. FIG. 4 (lower panel) shows the nucleotide sequence of the complete 3' end of the pJD67 plasmid DNA. Nucleotides denoted in upper case characters belong to the ARG7.8 gene. Nucleotides denoted in lower case characters belong to the 3' end of the vector sequence (pBR322). The underlined portion of the pJD67 3'end is also found in the cDNA nucleotide sequence obtained from the 5' RACE analysis of the tla1 mutant (FIG. 4, middle panel, lower case underlined nucleotides). Note that nine bases, i.e., a t t a a a g c t, at the 3' end of the full-length pJD67 (FIG. 4, lower panel) were deleted from the insertion site (FIG. 4, lower panel, black background). In sum, 187 bp of the 3' end of the pJD67 vector sequence have become the 5' UTR sequence of the Tla1 gene in the tla1 mutant, as they were amplified by the 5' RACE in the latter.

Complementation of the tla1 Mutant

Figure 5:
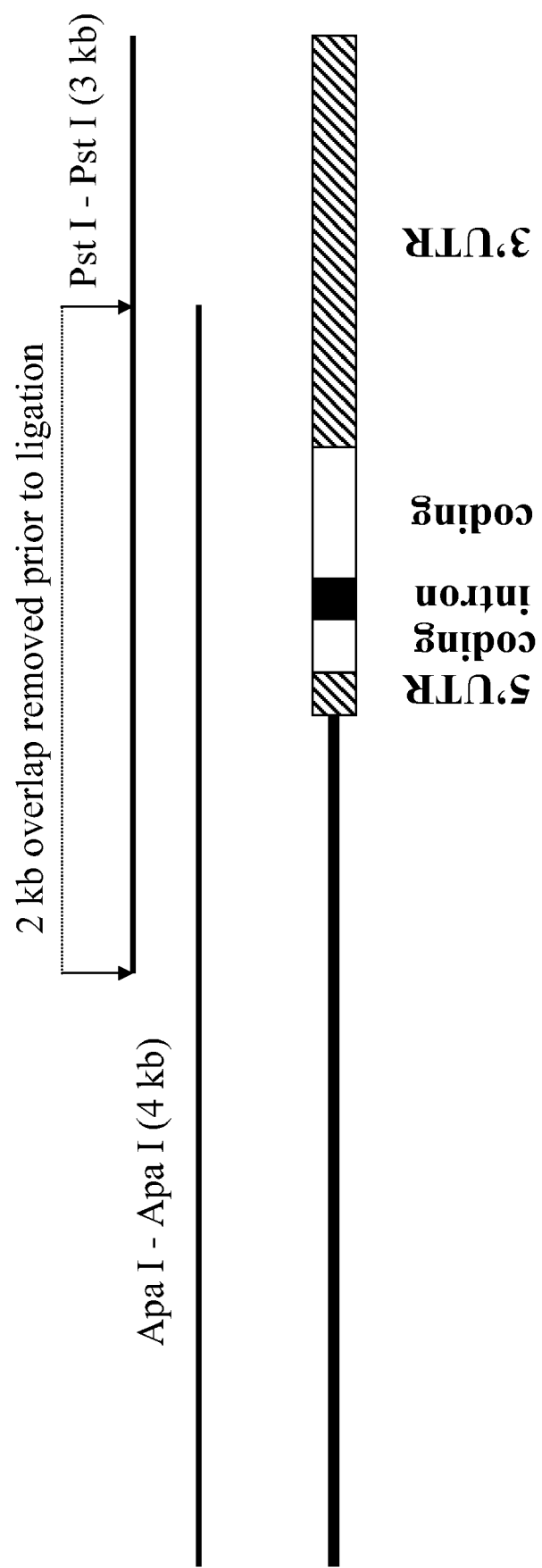
FIG. 5. Mapping of BAC clone 39e16 and subcloning of full length Tla1 gene for tla1 mutant complementation experiments. Southern blot analysis of the DNA from BAC clone 39e16 and subsequent DNA sequencing of subclones provided information on size and locus of a 3.7 kb Apa I-Apa I DNA fragment and a 3 kb Pst I-Pst I fragment. The 2 kb overlapping segment of the Pst I-Pst I fragment was removed. The remainder Pst I-Pst I piece was ligated onto the Apa I-Apa I DNA fragment and cloned in pBluescript to yield the 4.7 kb full length Tla1 gene on a single plasmid for use in complementation experiments.
Figure 6:
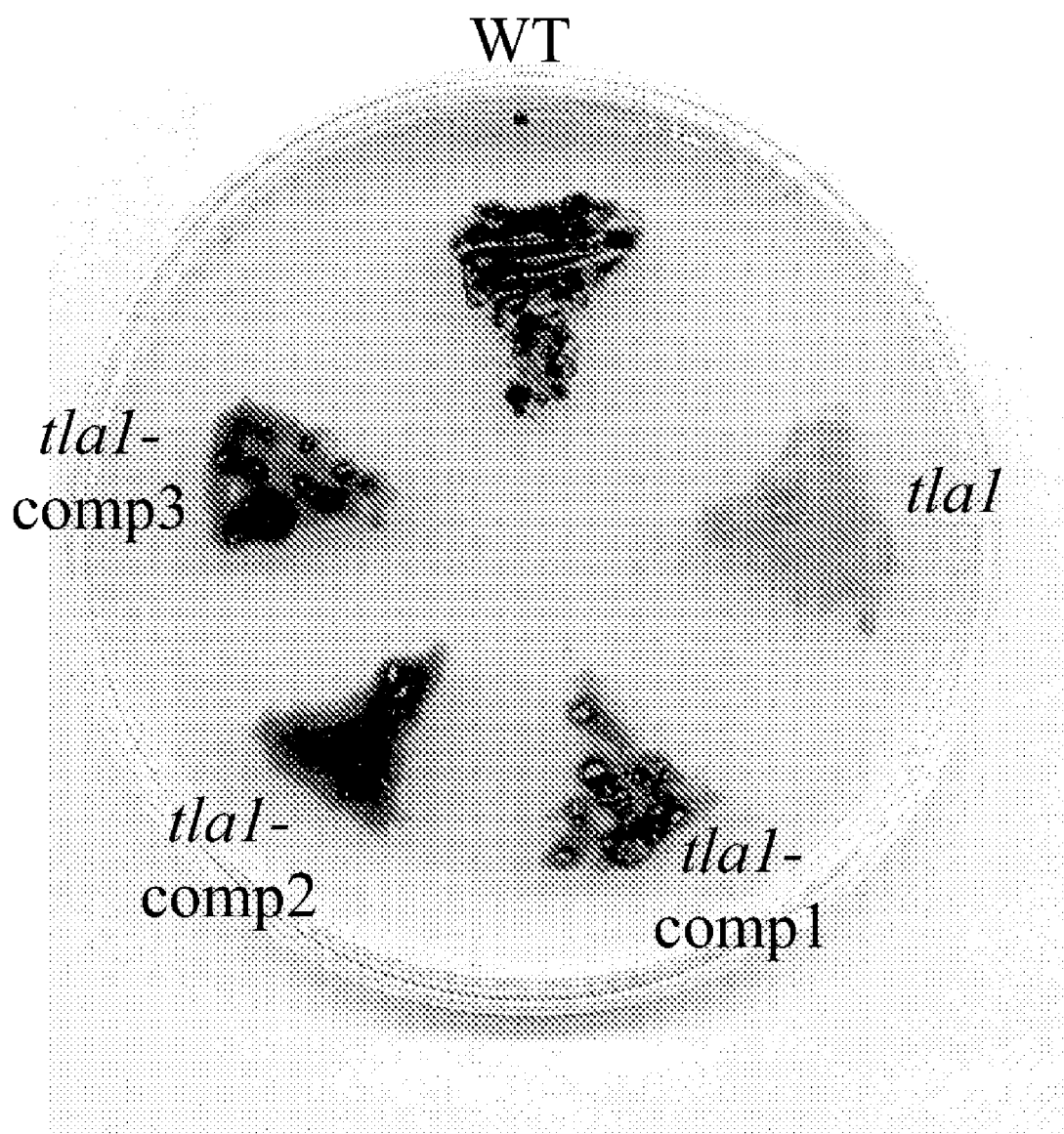
FIG. 6. TAP-Agar plate showing wild type (WT), tla1 mutant and complemented strains of the latter. Mutant strains were complemented with a copy of the wild type Tla1 gene. The phenotype of the tla1 mutant showed a faint green coloration, indicative of the low-level chlorophyll concentration in the cells, whereas the WT and putative complements 1, 2 and 3 were of about the same dark green coloration, indicating a greater Chl/cell.

A 4.7 kb genomic DNA, representing the full length Tla1 gene was cloned in pBluescript (FIG. 5). This plasmid was digested with Hind III and the Ble gene was added at the 5' end of the Tla1 gene to generate plasmid pSK9.2BleFTla1 (see Materials and methods). This plasmid was used to complement the tla1 mutant. Transformant colonies were selected on agar plates in the presence of 5 μM zeocin and screened for dark green coloration. Three dark green colonies, putative complements of the Tla1 gene were randomly isolated and streaked on to a TAP agar plate along with the wild type and tla1 mutant strains (FIG. 6). These putative complements, tla1-comp1, tla1-comp2 and tla1-comp3, showed wild type phenotype in terms of coloration and in vivo chlorophyll fluorescence induction kinetics. The putative complements were grown autotrophically in TBP medium and tested for the Chl/cell and Chl a/Chl b ratios.

Table 2 shows that wild type *C. reinhardtii* had a Chl a/Chl b ratio of 2.6, whereas the tla1 mutant had a Chl a/Chl b ratio of 6. The putative tla1-complemeted strains had much lower Chl a/Chl b ratios, ranging between 2.8-3.0. These values are much closer to that of the wild type than to the tla1 parental host strain. A lower Chl a/Chl b ratio suggests assembly of peripheral subunits of the Chl a-b light-harvesting complex, underlying an enlarged photosystem Chl antenna size (Polle, et al., *Plant Cell Physiol.* 42:482-491, 2001; and Polle et al., 2003, supra). Table 2 also shows the Chl/cell values of the various strains. Chl/cell in the wild type ($3.2 \times 10$-15 mol/cell) was substantially greater than that in the tla1 mutant ($1.1 \times 10^{-15}$ mol/cell). The complemented strains had Chl/cell values ($2.2$-$2.8 \times 10^{-15}$ mol/cell) comparable to that of the wild type, providing evidence of the return of the tla1-complemented strains to wild type levels of Chl content. Moreover, chlorophyll fluorescence induction kinetic measurements, with intact cells in the presence of DCMU, showed that the complemented strains, very much like the wild type, had a sigmoidal fluorescence rise curve, evidence of a statistical pigment bed organization afforded by a large Chl antenna size, as compared with the exponential fluorescence induction kinetics in the tla1 mutant (not shown). The lower Chl a/Chl b ratio, greater Chl/cell ratio (Table 2) and sigmoidal fluorescence induction kinetics in the Tla1-complemented strains are evidence of a direct cause-and-effect relationship between the amount of the Tla1 protein and the amount of chlorophyll in *C. reinhardtii*. Thus, it is concluded that the Tla1 gene regulates the Chl antenna size of photosynthesis in this model green alga.

TABLE 2

Chl a/Chl b ratio and Chl content per cell in *C. reinhardtii* wild type (WT), tla1 mutant and tla1 mutant complemented with the Tla1 gene (comp1–3). Statistical error (+/−SD) was <10% of the values shown.

| Strain | Chl a/Chl b ratio | Chl, $\times 10^{-15}$ mol/cell |
|---|---|---|
| WT (cw15) | 2.6 | 3.2 |
| tla1 | 6.0 | 1.1 |
| tla1-comp1 | 2.9 | 2.8 |
| tla1-comp2 | 3.0 | 2.2 |
| tla1-comp3 | 2.8 | 2.4 |

Example 2

Tla1 Gene Expression is Reduced in the tla1 Mutant Strain

Figure 7:
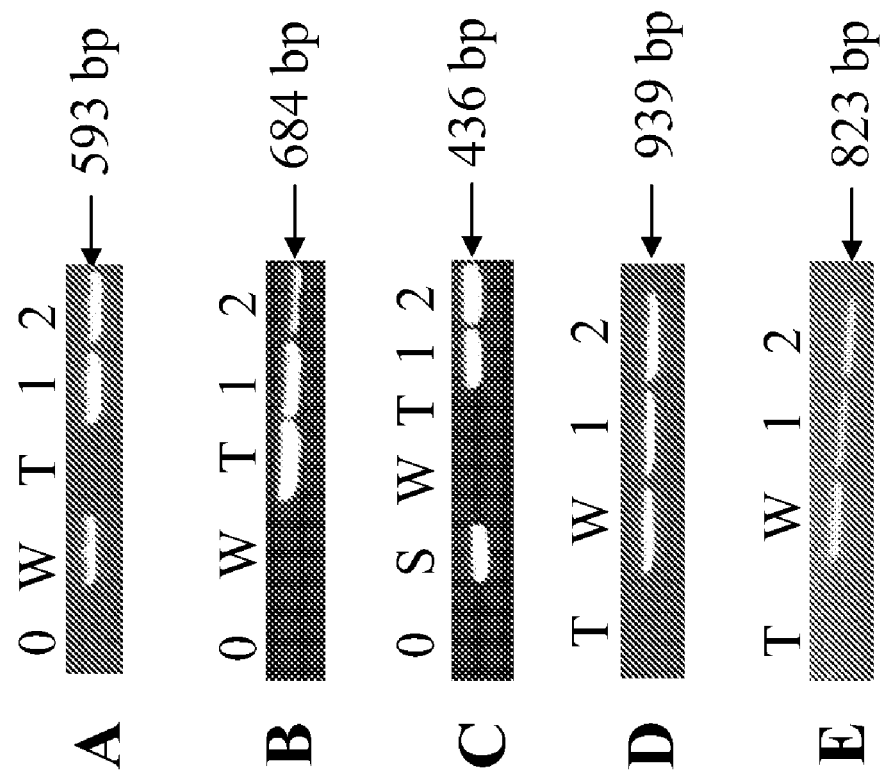
FIG. 7. PCR analysis using genomic DNA of wild type and tla1 complements. (A)PCR product of 593 bp obtained with "primer 1" and "primer 4" (Tla1 promoter/Exon-2) primers. (B) PCR product of 684 bp obtained with "primer 7" and "primer 4" (pJD67 3' end/Tla1 Exon-2) primers. (C) PCR product of 436 bp obtained with "primer 8" and "primer 9" (Ble gene) primers. (D) PCR product of 939 bp obtained with "primer 1"and "primer 6" (Tla1 promoter/3'UTR) primers. (E) RT-PCR analysis of tla1 complements. PCR product of 823 bp obtained when "primer 1" and "primer 6" (Tla1 5'UTR/3'UTR) specific primers were used. "0", "W", "T", "1", "2" and "S" stand for zero DNA, wild type, tla1 mutant, tla1-comp1, tla1-comp2 and pSP124s plasmid containing the Ble gene, respectively.

In the subsequent more detailed biochemical and molecular analyses, a comparative and quantitative evaluation of wild type, tla1 mutant, tla1-comp1 and tla1-comp2 was undertaken. When PCR was performed on the genomic DNA using "primer 1" and "primer 4" (Tla1 5'UTR/Exon-2, FIGS. 2A and 2C) wild type, tla1-comp1 and tla1-comp2 yielded a 589 bp product, whereas the tla1 mutant failed to yield a product, consistent with the absence of its 5'UTR region (FIG. 7A). When "primer 7" and "primer 4" (pJD67 3' end/ Tla1 Exon-2, FIG. 2B) were used in the PCR reaction, the tla1 mutant, tla1-comp1 and tla1-comp2 generated a product of 684 bp whereas the wild type did not, consistent with the absence of the pJD67 plasmid in the latter (FIG. 7B). When Ble primers, "primer 8" and "primer 9" (FIG. 2C) were used for the genomic DNA PCR reaction, tla1-comp1 and tla1-comp2 yielded a product of 436 bp, whereas both wild type and tla1 mutant failed to generate a product (FIG. 7C). PCR was also employed to test for the presence of the intact full length Tla1 gene in the two complements using the "primer 1" and "primer 6" (Tla1 5'UTR/Tla1 3'UTR, FIG. 2A). Wild type, tla1-comp1 and tla1-comp2 gave a product of 939 bp whereas the tla1 mutant did not yield a product (FIG. 7D). When the same primers were used to perform RT-PCR, wild type, tla1-comp1 and tla1-comp2 gave a product of 823 bp, whereas the tla1 mutant did not yield a product (FIG. 7E). These results are evidence of successful complementation of the tla1 mutant by the ble-Tla1 construct.

Western Blot Analysis with Tla1-Specific Antibodies in Wild Type tla1 Mutant and Tla1 Complemented Strains

Figure 8:
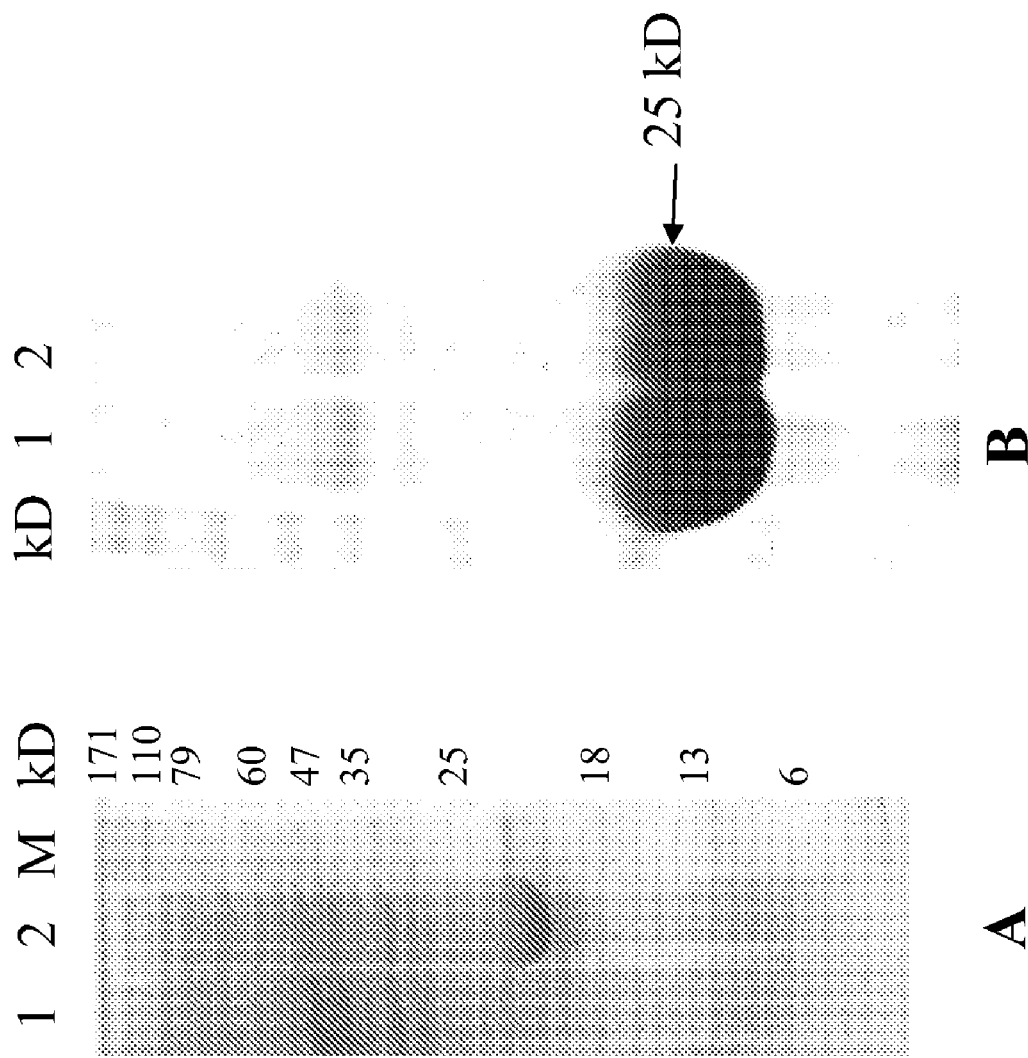
FIG. 8. Overexpression and purification of recombinant Tla1 protein. A 12.5% SDS-PAGE gel stained with Coomassie blue showing: (A) Un-induced (lane 1) and induced (lane 2) E. coli cells expressing the recombinant 6*His-Tla1 protein. 20 μg of total E. coli cell protein extracts were loaded on each lane. "M" denotes unstained Benchmark low molecular weight markers. (B) Purified 6*His-Tla1 protein fractions (lanes 1 and 2). 35 μg of purified recombinant protein was loaded in each lane. "M" denotes the Benchmark pre-stained low molecular weight markers FIG. 9. Immune serum titer and Tla1 protein immunodetection in wild type and tla1 mutant. (A) A Western blot of isolated recombinant Tla1 protein (6*His-Tla1), probed with Tla1-specific antibodies. Lanes 1, 2 and 3 contain 20 ng, 20 pg and 2 pg of purified recombinant Tla1 protein, respectively. (B) SDS-PAGE stained with Coomassie blue showing the total protein profile of wild type (W) and tla1 mutant (T) of C. reinhardtii. Lanes were loaded on an equal-Chl basis (6 nmol Chl per lane). "M" stands for the Benchmark pre-stained low molecular weight markers. (C) Western blot analysis of wild type (W) and tla1 (T) total cell protein extracts from C. reinhardtii, probed with Tla1-specific polyclonal antibodies. Lanes were loaded on an equal-Chl basis (6 nmol Chl per lane).

*E. coli* cells harboring the recombinant 6* His-Tla1 construct were induced for 5 h at 37° C. to overexpress the His-tagged Tla1 fusion protein. The overexpressed recombinant Tla1 protein comprised approximately 20% of the total *E. coli* protein (FIG. 8A). The recombinant fusion protein was purified by one-step affinity chromatography using Ni-NTA superflow columns and further concentrated by a passage through Centricon columns. Purification of the 25 kD fusion protein was confirmed by SDS-PAGE and Coomassie staining (FIG. 8B).

Figure 9:
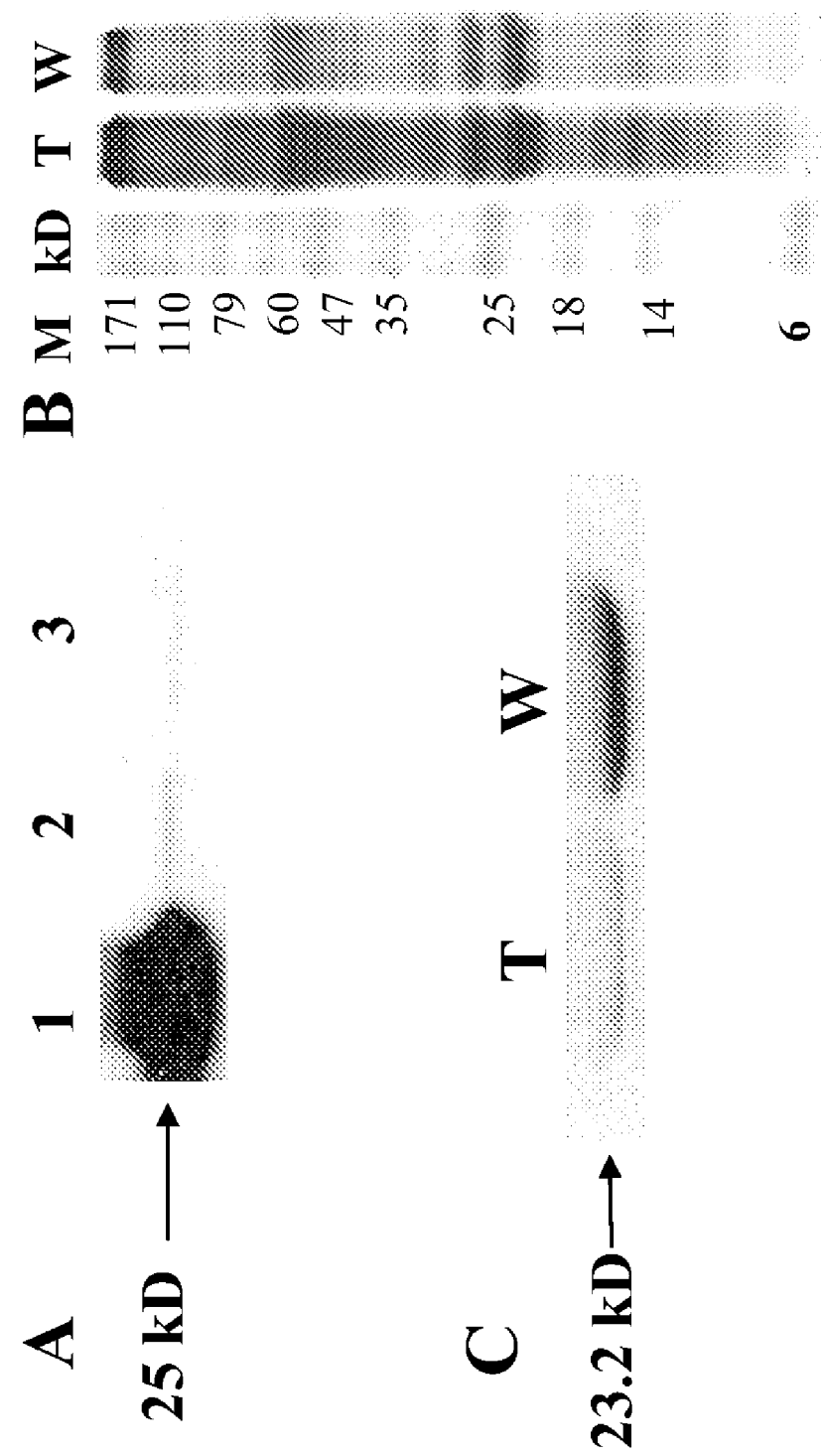

Tla1 specific polyclonal antibodies positively cross-reacted with the purified 25 kD recombinant Tla1 protein and at levels as low as 2 pg (FIG. 9A). Whereas the molecular weight of the native Tla1 protein is 23.2 kD, the recombinant protein was slightly larger (25 kD) because of the extra seventeen amino acids, including the 6 * His (SEQ ID NO:33) tag, at its N-terminal end.

Total cell extract from wild type (CC425) and the tla1 mutant were loaded on a 12.5% SDS-PAGE gel on an equal chlorophyll basis (FIG. 9B). Tla1 antibodies detected the 23.2 kD Tla1 protein in the total protein extract from the wild type and tla1 mutant (FIG. 9C). The amount of the Tla1 protein was substantially lower in the tla1 mutant compared to that in the wild type (FIG. 9C). This provides evidence that a limited translation of the tla1 mRNA did occur in the mutant, however, this is in no way comparable to the levels of translation seen in the wild type. The substantially suppressed translation level of the Tla1 protein in the tla1 mutant is attributed to the absence of the native 5'UTR in this strain. The apparent molecular weight of the Tla1 protein is the same in WT and tla1 mutant (FIG. 9C). This observation is consistent with the notion that the wild type Tla1 protein lacks a transit peptide and is apparently a cytoplasmic protein.

Figure 10:
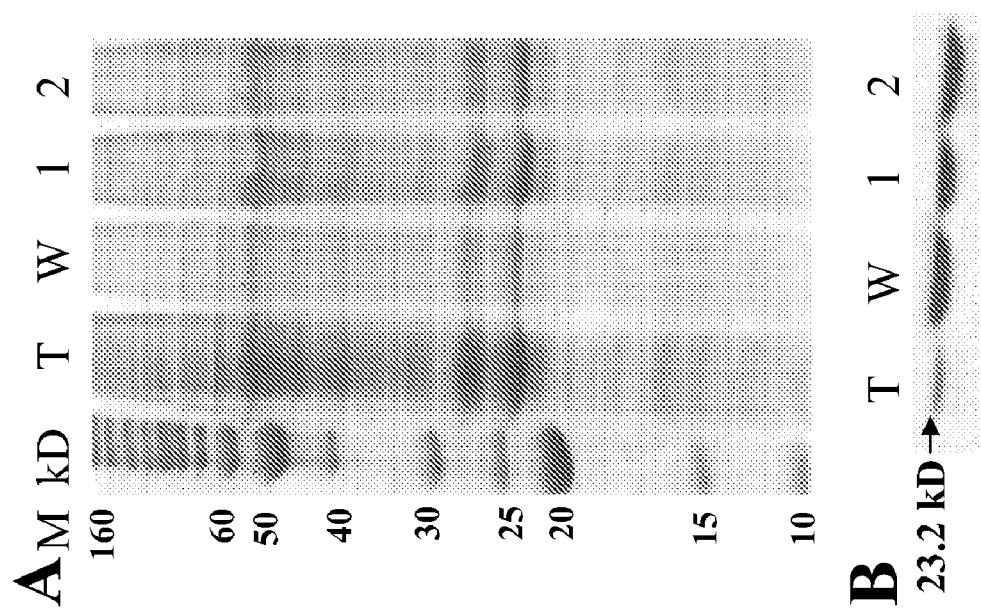
FIG. 10. SDS-PAGE and Western blot analysis of wild type, tla1 mutant and tla1 complemented strains. (A) SDS-PAGE of C. reinhardtii total cell protein extracts from wild type (W), tla1 mutant (T), and tla1 complements comp1 (lane 1) and comp2 (lane 2). Lanes were loaded on an equal-Chl basis (4 nmol Chl per lane). "M" stands for the unstained Benchmark low molecular weight markers. (B) Western blot analysis of C. reinhardtii total cell protein extracts from wild type (W), tla1 mutant (T), and tla1 complements, tla1-comp1 (lane 1) and tla1-comp2 (lane 2), probed with Tla1-specific polyclonal antibodies.

Total protein extracts from the wild type, tla1 mutant and two tla1 complements (tla1-comp1 and tla1-comp2) were resolved on a 12.5% SDS-PAGE gel, lanes loaded on an equal chlorophyll basis (FIG. 10A). Western blot analysis of the total cell extract from these samples showed that the amount of the Tla1 protein in the two complements (FIG. 10B, lanes 1 and 2) was comparable to that in the wild type (FIG. 10B, W), whereas the amount of the Tla1 protein in the tla1 mutant was substantially lower from that of the other three (FIG. 10B, lane T).

Example 3

Analysis of Tla1 Protein

Hydropathy Analysis of the Tla1 Protein

Figure 11:
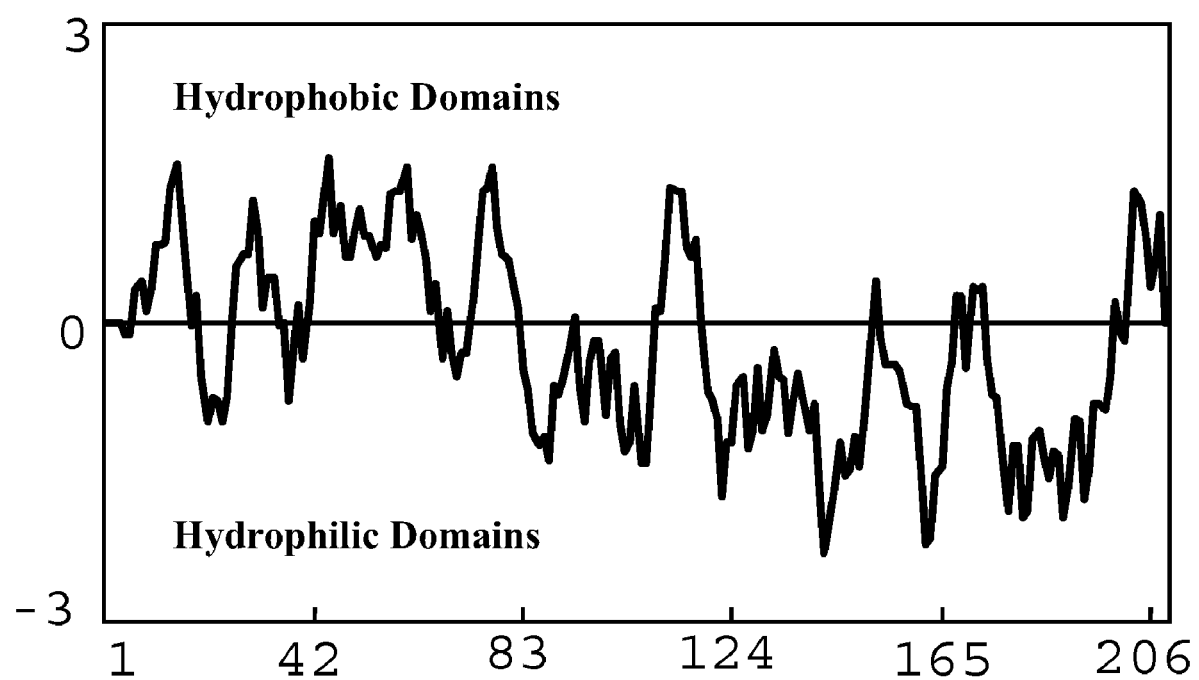
FIG. 11. Hydropathy plot of the Tla1 deduced amino acid sequence. The X-axis plots the 213 amino acids of the Tla1 protein, whereas the Y-axis plots the respective amino acid hydropathy index. Positive hydropathy index corresponds to hydrophobic domains of the protein whereas a negative hydropathy index corresponds to hydrophilic polypeptide domains.

Analysis of the N-terminus sequence of the predicted Tla1 protein by ChloroP, (http://www.cbs.dtu.dk/services/ChloroP/), TargetP (http://www.cbs.dtu.dk/services/TargetP/) and MitoP (http://ihg.gsf.de/ihg/mitoprot.html) software programs failed to indicate the presence of a transit peptide, suggesting that Tla1 is a cytosolic protein. This indication was strengthened by the results of the Western blot analysis, where the mature protein size matched the predicted translation product size, suggesting absence of a cleavable transit peptide. FIG. 11 shows the hydropathy plot of the deduced amino acid sequence of the Tla1 protein, derived according to the method of Kyte & Doolittle (Kyte and Doolittle, *J Mol Biol.* 157:105-32982, 1982; http://occawlonline.pearsoned.com/bookbind/pubbooks/bc_mcampbell_genomics_1/medialib /activities/kd/kyte-doolittle.htm). The Tla1 protein contains 213 mostly hydrophilic amino acids, suggesting that it is a soluble cytosolic protein. There was a single hydrophobic domain comprising 27 amino acids between residues 42 and 69, theoretically long enough to qualify as a transmembrane domain. This hydrophobic domain of 27 amino acids is highly conserved in similar proteins from other diverse organisms, suggesting a role in the catalytic/regulatory activity of the Tla1 protein.

Tla1 Homology with Genes from Other Organisms

A Blastp (protein database using protein sequence) search showed high homology of the Tla1 protein with expressed protein sequences of *Arabidopsis thaliana* (GenBank Accession No. NP_568832) *Oryza sativa* (japonica cultivar-group) (Accession No. CAD39888) *Ustilago maydis* (Accession No. EAK83164), *Drosophila melanogaster* (Accession No. NP_611731), *Homo sapiens* (Accession No. AAQ83690), *Danio rerio* (zebrafish) (Accession No. NP_956420), *Rattus norvegicus* (Norway rat) (Accession No. XP_214198), *Xenopus tropicalis* (Accession No. NP_989181), *Mus musculus* (house mouse) (Accession No. NP_035056). In view of the *Chlamydomonas reinhardtii* specific codon usage, we also searched nucleotide databases using the Tla1 protein sequence (tblastn-protein query against translated database). EST sequences deposited from several other plant species showed fairly high homology with the Tla1, including sequences from *Hordeum vulgare, Solanum tuberosum, Medicago truncatula, Lycopersicon esculentum, Gossypium arboretum, Secale cereale, Triticum aestivum, Pinus taeda, Beta vulgaris, Populus tremula, Sorghum bicolor* (results not shown). It is concluded that the Tla1 gene is present in many eukaryotes, including many wild-land and crop plants.

FIG. 12A shows an alignment of the deduced amino acid sequence of the Tla1 protein from *C. reinhardtii* alongside that of proteins from *A. thaliana, O. sativa, H. sapiens* and *D. melanogaster*. The sequence alignment in FIG. 12A shows very high similarity between the Tla1 protein in *C. reinhardtii* and the related proteins in these diverse organisms. Moreover, examination of identity/similarity patterns in FIG. 12A, based on the ClustalW analysis, revealed the common occurrence of domains where high similarity or identity of amino acids is observed. The highly conserved nature of these domains across diverse species suggest a common functional role for these proteins.

Figure 12B:
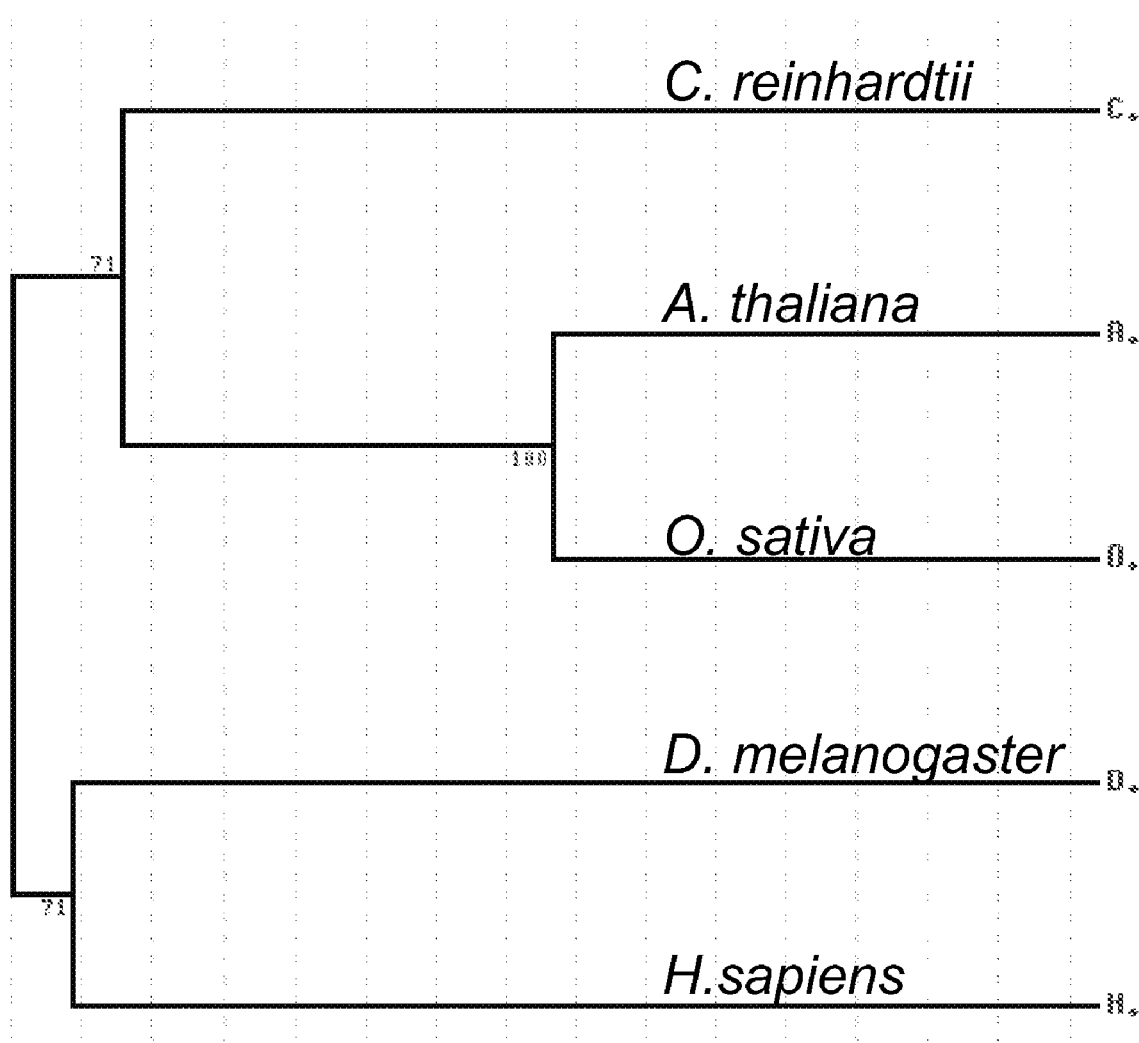
FIG. 12. (A) Alignment of Tla1-like proteins from different organisms. The alignment of the Tla1 deduced amino acid sequence of C. reinhardtii is compared to that of similar proteins from A. thaliana (SEQ ID NO:19), O. sativa (SEQ ID NO:20), H. sapiens CGI 112 protein, (SEQ ID NO:21), and D. melanogaster (SEQ ID NO:22 ). Four polypeptide domains with high sequence conservation can be deduced from this comparison. The alignment was done on the basis of the ClustalW web-based software (http://www.ch.embnet.org/software/ClustalW.html). (B) Phylogenetic comparison of putative Tla1 homologue proteins encoded by genes from a variety of organisms. The phylogenetic tree of the above-shown proteins was based on the deduced amino acid sequences ((http://www.ebi.ac.uk/clustalw).

These related protein sequences were also aligned pairwise and degrees of identity, high and low similarity were calculated on the basis of a ClustalW comparison. Results from such analyses (Table 3) showed that the *C. reinhardtii* Tla1 protein had a 72.68% homology to the corresponding protein in *A. thaliana,* 75.99% homology to *O. sativa,* 70.94% to *D. melanogaster* and 67.14% to *H. sapiens* (CGI-112). FIG. 12B shows a phylogenetic tree of the above-mentioned Tla1 homologues, based on the amino acid sequence comparisons http://www.ebi.ac.uk/clustalw/).

TABLE 3

Homology comparison of Tla1-like proteins in *Chlamydomonas reinhardtii, Arabidopsis thaliana, Oryza sativa, Drosophila melanogaster* and *Homo sapiens.* The % of amino acid identity, high similarity and low similarity was based on a ClustalW analysis of the deduced amino acid sequence of the respective proteins.

| Pair compared | % Identity | High similarity | Low similarity | % Homology |
| --- | --- | --- | --- | --- |
| C.r.-A.t. | 35.62 | 23.75 | 13.31 | 72.68 |
| C.r.-O.s.. | 38.27 | 23.92 | 13.8 | 75.99 |
| C.r.-D.m. | 30.54 | 23.15 | 17.24 | 70.94 |
| C.r.-H.s. | 28.09 | 24.76 | 14.28 | 67.14 |

Summary

The ability of the photosynthetic apparatus to regulate the size of the functional Chl antenna was first recognized in pioneering work by Bjorkman and co-workers, more than 30-years ago (Bjorkman et al., *Carnegie Institution Yearbook* 71:115-135, 1972). In spite of the substantial number of physiological and biochemical studies on this phenomenon (reviewed Anderson, *Annu Rev Plant Physiol* 37:93-136, 1986; Melis, In, *Oxygenic Photosynthesis: The Light Reactions*" (DR Ort, CF Yocum, eds), Kluwer Academic Publishers, Dordrecht, The Netherlands, pp. 523-538, 1996), genes for the regulation of the Chl antenna size of photosynthesis have not been identified. The current invention is based on the discovery that Tla1 plays a role in the regulation of the chlorophyll antenna size of photosynthesis. Not to be bound by theory, Tla1 is likely to regulate the expression of other genes that directly affect the chloroplast and the Chl antenna size and may define the relationship between nucleus and organelle in green algae, thereby regulating the rate of Chl biosynthesis and by extension the Chl antenna size of the photosystems. For example, in the tla1 mutant, total amount of Chl, Lhcb gene expression, abundance of LHC polypeptides, and levels of Chl b were all down regulated (Table 2), presumably as a consequence of down-regulation of translation of the Tla1 mRNA. Sensitive absorbance-difference kinetic spectrophotometry confirmed that the tla1 mutant had a truncated PSII Chl antenna size, down to 50%, and a truncated PSI Chl antenna size, down to 67% of that in the wild type (Polle et al. 2003, supra). Thus, in the tla1 mutant, the Chl antenna size of both photosystems, as well as total chlorophyll per cell were lowered relative to the wild type.

Further evidence for the role of the Tla1 gene in the regulation of the Chl antenna size of photosynthesis was obtained from the study of *C. reinhardtii* diploid analysis and from Tla1 complementation studies. Diploid analysis showed that the tla1 mutation is recessive (results not shown). About 25 diploids were tested, all of which showed WT phenotype in terms of normal green coloration of the colonies, normal Chl fluorescence and normal Chl a to Chl b ratio (in the range of 2.2-3.0) as opposed to the tla1 mutant phenotype of yellow-green coloration, lower Chl fluorescence and higher Chl a to Chl b ratio. The results of the diploid analysis served as the basis upon which a functional complementation of the tla1 mutant was undertaken. This was successfully implemented (FIGS. 6 and 7) upon transformation of the tla1 strain with a WT copy of the Tla1 gene, containing about a 4.7 kb DNA sequence comprising the promoter region and its 5' flanking sequence, the 5' UTR, the coding sequence with a single intron, and the 3' UTR region of the Tla1 gene.

Sequence analysis of the 3'-insert flanking sequence from the tla1 mutant revealed that the 3' end of the plasmid was inserted within the *C. reinhardtii* genomic DNA, just prior to the ATG start codon of the Tla1 gene. In spite of the absence of the promoter and 5'UTR region of the Tla1 gene and the presence of a sizable plasmid insertion just prior to the 'ATG' start codon of the Tla1 gene, RT-PCR analysis (FIG. 3) revealed the presence of Tla1 transcripts in the tla1 mutant. One possible explanation of this unusual observation is that, in the tla1 mutant, the Tla1 gene is co-transcribed along with the ARG7 gene under the control of the ARG7 gene promoter. Northern blot analyses, using the coding region of the Tla1 gene as a probe, revealed similar the Tla1-transcript size from both WT and tla1 mutant (results not shown). High molecular weight transcripts of the Tla1 gene could not be detected in the tla1 mutant, as would be expected from the unprocessed ARG7-Tla1 hybrid transcripts.

From the above characteristics (tla1 phenotype, diploid properties, complementation of the tla1 mutant with wild type Tla1 gene, and presence of Tla1 transcripts in the tla1 mutant), it is concluded that transcription of the Tla1 gene occurs in the tla1 mutant but translation of the respective mRNA is either impaired or minimized. Polymorphism in the 5' UTR of the Tla1 gene has not measurably affected its mRNA stability since levels of these transcripts detected by Northern blot (data not shown) and RT-PCR analysis were the same in both the wild type and mutant. However, it has had a substantial effect on the rate of translation of the respective mRNAs, as evidenced from the Western blot analysis results. In the tla1 mutant, the 5'UTR consists of 187 bp sequences from the 3'end of the plasmid pJD67. Normally, the eukaryotic translation machinery does not recognize prokaryotic sequences. This could explain the much lower translation levels of the Tla1 mRNA in the mutant relative to that in the wild type.

It is apparent from these data that in green unicellular algae the Tla1 gene acts as an early component affecting the molecular regulatory mechanism for the Chl antenna size in of oxygenic photosynthesis. A genetic tendency of the algae to assemble large arrays of light absorbing chlorophyll antenna molecules in their photosystems is a survival strategy and a competitive advantage in the wild, where light is often limiting (Kirk, *Light and photosynthesis in aquatic ecosystems*, 2nd edn. Cambridge University Press, Cambridge, England, 1994). This property of the algae is detrimental to the yield and productivity in a mass culture under direct sunlight (Melis, *Trends in Plant Science* 4: 130-135, 1999), however. A truncated Chl antenna size, which would compromise the ability of the strain to compete and survive in the wild, is helpful in a controlled mass culture environment in photoreactors in diminishing the over-absorption and wasteful dissipation of excitation energy by individual cells. The size reduction of the Chl antenna will also diminish photoinhibition of photosynthesis (Powles, *Annu Rev Plant Physiol* 35: 15-44, 1984; Melis, 1999, supra) at the surface while permitting for greater transmittance of light deeper into the culture (Melis, 2005, supra). Such altered optical properties of the cells result in greater photosynthetic productivity and enhanced solar conversion efficiency by the culture as a whole. In support of this contention, preliminary experiments (Powles, *Annu Rev Plant Physiol* 35: 15-44, 1984) confirmed that a smaller Chl antenna size would result in a relatively higher light intensity for the saturation of photosynthesis in individual cells, while permitting for an overall greater solar conversion efficiency and productivity by the mass culture (Powles, *Annu Rev Plant Physiol* 35: 15-44, 1984). Thus, the Tla1 gene can be useful as a target to down-regulation Chl antenna size, e.g., in green microalgae.

The above examples are provided by way of illustration only and not by way of limitation. Those of skill in the art will readily recognize a variety of noncritical parameters that could be changed or modified to yield essentially similar results.

All publications, accession numbers, and patent applications cited in this specification are herein incorporated by reference as if each individual publication or patent application were specifically and individually indicated to be incorporated by reference.

Table of Exemplary Tla1 Nucleic Acid and Polypeptide Sequences

```
  1   ggaacctcga tgtcgtgttg actttgcgtt acaaccgtga
      agtatattag aactcatttg 61   cctgccacaa cctcagacca agagacgcgc gaaaaactga
      cacgatgact ttcagctgct 121   ccgctgacca aaccgcgctc ttaaagattc ttgcacacgc
      ggctaagtat ccatcaaata 181   gcgtgaatgg tgtcctcgtc gggacagcga aggagggcgg
      ctctgtcgaa atcctggacg 241   cgattccact gtgtcacacg acgctgaccc tggcgccagc
      actggagata ggtctcgccc 301   aggtggagtc ctacacgcat atcacgggca gcgtggcgat
      tgtgggctac taccaatcag 361   acgcacgttt cggccccggg gacctacccc cgctaggtcg
      caaaattgcg gacaaggtgt 421   ctgagcacca ggctcaggcg gtggtgctgg tgctggacaa
      caagcggctg gagcagttct 481   gcaaggcgca ggcggacaac ccgttcgagc tgttcagcaa
      ggatggcagc aagggttgga 541   agcgcgcgag cgccgatggc ggagagctgg cgcttaaaaa
      cgcggactgg aagaagctgc 601   gcgaggagtt cttcgttatg ttcaagcagc tgaagcaccg
      gacactccac gattttgagg 661   agcacctgga cgacgccggg aaagactggc tcaacaaggg
      cttcgcctcc tcggtcaaat 721   tcctgttgcc cggcaacgcg ctgtaagggc cgcgtgaggc
      tagccgggat ggcggttccg
```

-continued

```
 781 cgggatggtc gcagtgccgg ggtgtgtgtt gagaggagga
     gccggtgggg gggaaagagg 841 ttgaggaggt aggagagagg cgctggcatg gaggccggga
     ggcgctggag ctggagctgg 901 cgagctggtg ggtggtgctg ggcgagatcc tggaggcaca
     ggagtggtat gggcggtgca 961 gggacagcga cagcggatcg gcggacggta ttggtggagg
     gtgcggggc cctggggtag 1021 tgtgcagggt gtgtgccacg tggcttgccg caaagcgcag
     cgtaccgata gttgagagaa 1081 agcacctgcg gccctgcgcg gccgcggcgt ggcggcgcgt
     ggggacacgc gcatcgtgcc 1141 gggtcgccgc aggccggagt gaatttcgtg ctgcacggcg
     cgttgaccag tccaccgact 1201 gacggccaac ggccatgagg gcttgttttg ggggatgggg
     tcacatgaca ttttcggcgt 1261 tctttgcagt cagaatcagg atacgcttgc tttagtcttg
     attgtcagac ttgtcaggct 1321 gacgtttcag gcagacgaga gctcatgtgg ttttgactaa
     ccgggcgttg accatgggca 1381 gtcccaaacg tgccgtgcca cagggcatag cgagtgccat
     gtgctctcga gggcgaggtc 1441 gtgaggcacg tggaaactgt tgcggcgcct tcaccatggg
     tgctttctcg cgtgaggcac 1501 gtgaaactgt tgcggcgcct tcaccatggg tgctctctct
     cgtgaggctc agcggcaagt 1561 accagggagg gcgcaagaca cggatgaagc agtggttgcg
     catgccgcgg tctgttggcc 1621 gccgggaggt gatcggtgtg acgtggctgg tgcgtgtggt
     ggtttctccc gtggcctccc 1681 gtgtgtgact ggtgcgtgtt tgacgtggca aggtaggtaa
     atagtagtaa agcggcccag 1741 atacgttgct gtggcggttg tgcgtgcgca ggtggtgcat
     aggacagcgt tggttgtgtg 1801 tgcctgtgct gtgctgtgcg gtgccggacc gaagcgcggg
     gcggacaggc gcagggtggt 1861 agcggcgtgg cgggtaggct gccgcacaca gtacgtgtaa
     ctgtatgctg cgctgcatgt 1921 tactctgctt acggatgctt cctgactgta cgtgtggtgc
     ttgggtcgtg tcgccgtgca 1981 acgctgctgg cggcttcaat gggtggctgc ggatcagtgg
     gtggctgcgt gtatcggcgc 2041 gcccgtgttg aatcgaggac tgcag
```

SEQ ID NO:2 Tla1 Polypeptide Sequence

MTFSCSADQTALLKILAHAAKYPSNSVNGVLVGTAKEGGSVEILDAIPLC
HTTLTLAPALEIGLAQVESYTHITGSVAIVGYYQSDARFGPGDLPPLGRK
IADKVSEHQAQAVVLVLDNKRLEQFCKAQADNPFELFSKDGSKGWKRASA
DGGELALKNADWKKLREEFFVMFKQLKHRTLHDFEEHLDDAGKDWLNKGF
ASSVKFLLPGNAL

Conserved Domains: (SEQ ID NOS:24-28):

Domain A: amino acid positions 9-33
(QTALLKILAHAAKYPSNSVNGVLVG)

Domain B: amino acid positions 41-70
(VEILDAIPLCHTTLTLAPALEIGLAQVESY)

Domain C: amino acid positions 75-129
(GSVAIVGYYQSDARFGPGDLPPLGRKIADKVSEHQAQAVVLVLDNKRLE
QFCKAQ)

Domain D: amino acid positions 135-163
(ELFSKDGSKGWKRASADGGELALKNADWK)

Domain E: amino acid positions 177-200
(KHRTLHDFEEHLDDAGKDWLNKGF)

SEQ ID NO:3 Tla1 Genomic Sequence

```
   1 ggaacctcga tgtcgtgttg actttgcgtt acaaccgtga
     agtatattag aactcatttg 61 cctgccacaa cctcagacca agagacgcgc gaaaaactga
     cacgatgact ttcagctgct 121 ccgctgacca aaccgcgctc ttaaagattc ttgcacacgc
     ggctaagtat ccatcaaata 181 gcgtgaatgt tgtcctcgtc gggacagcga aggagggcgg
     ctctgtcgaa atcctggacg 241 cgattccact gtgtcacacg acgctgaccc tggcgccagc
     actggagata ggtctcgccc 301 aggtgcgcat ggccccgaga gcccggggcg tggcttgtgc
     tcgtcgatct gcgtgcatta 361 gttaccgcat cgctcccatg ctgcattccg cgctcagcct
     caaataccct gattgcaggt 421 ggagtcctac acgcatatca cgggcagcgt ggcgattgtg
     ggctactacc aatcagacgc 481 acgtttcggc cccggggacc tacccccgct aggtcgcaaa
     attgcggaca aggtgtctga 541 gcaccaggct caggcggtgg tgctggtgct ggacaacaag
     cggctggagc agttctgcaa 601 ggcgcaggcg gacaacccgt tcgagctgtt cagcaaggat
     ggcagcaagg gttggaagcg 661 cgcgagcgcc gatggcggag agctggcgct taaaaacgcg
     gactggaaga agctgcgcga 721 ggagttcttc gttatgttca agcagctgaa gcaccggaca
     ctccacgatt ttgaggagca 781 cctgacgac gccgggaaag actggctcaa caagggcttc
     gcctcctcgg tcaaattcct 841 gttgcccggc aacgcgctgt aagggccgcg tgaggctagc
     cgggatggcg gttccgcggg 901 atggtcgcag tgccggggtg tgtgttgaga ggaggagccg
     gtgggggga aagaggttga 961 ggaggtagga gagaggcgct ggcatggagg ccggaggcg
     ctggagctgg agctggcgag 1021 ctggtgggtg gtgctgggcg agatcctgga ggcacaggag
     tggtatgggc ggtgcaggga 1081 cagcgacagc ggatcggcgg acggtattgg tggagggtgc
     gggggccctg gggtagtgtg 1141 cagggtgtgt gccacgtggc ttgccgcaaa gcgcagcgta
     ccgatagttg agagaaagca
```

```
1201 cctgcggccc tgcgcggccg cggcgtggcg gcgcgtgggg
     acacgcgcat cgtgccgggt 1261 cgccgcaggc cggagtgaat ttcgtgctgc acggcgcgtt
     gaccagtcca ccgactgacg 1321 gccaacggcc atgagggctt gttttggggg atagggtcac
     atgacatttt cggcgttctt 1381 tgcagtcaga atcaggatac gcttgcttta gtcttgattg
     tcagacttgt caggctgacg 1441 tttcaggcag acgagagctc atgtggtttt gactaaccgg
     gcgttgacca tgggcagtcc 1501 caaacgtgcc gtgccacagg gcatagcgag tgccatgtgc
     tctcgagggc gaggtcgtga 1561 ggcacgtgga aactgttgcg gcgccttcac catgggtgct
     ttctcgcgtg aggcacgtga 1621 aactgttgcg gcgccttcac catgggtgct ctctctcgtg
     aggctcagcg gcaagtacca 1681 gggagggcgc aagacacgga tgaagcagtg gttgcgcatg
     ccgcggtctg ttggccgccg 1741 ggaggtgatc ggtgtgacgt ggctggtgcg tgtggtggtt
     tctcccgtgg cctcccgtgt 1801 gtgactggtg cgtgtttgac gtggcaaggt aggtaaatag
     tagtaaagcg gcccagatac 1861 gttgctgtgg cggttgtgcg tgcgcaggtg gtgcatagga
     cagcgttggt tgtgtgtgcc 1921 tgtgctgtgc tgtgcggtgc cggaccgaag cgcggggcgg
     acaggcgcag ggtggtagcg 1981 gcgtggcggg taggctgccg cacacagtac gtgtaactgt
     atgctgcgct gcatgttact 2041 ctgcttacgg atgcttcctg actgtacgtg tggtgcttgg
     gtcgtgtcgc cgtgcaacgc 2101 tgctggcggc ttcaatgggt ggctgcggat cagtgggtgg
     ctgcgtgtat cggcgcgccc 2161 gtgttgaatc gaggactgca g
```

---

What is claimed is:

1. A method of decreasing chlorophyll antenna size in a strain of green algae, the method comprising:

inhibiting expression of a Tla1 nucleic acid in the green algae strain by introducing into the green algae strain an expression cassette comprising a promoter operably linked to a polynucleotide, or a complement thereof, wherein the polynucleotide is at least 90% identical to at least 200 contiguous nucleotides of a nucleic acid sequence encoding SEQ ID NO:2; or comprises at least 20 contiguous nucleotides of SEQ ID NO:1 or SEQ ID NO:3; and selecting algae with decreased chlorophyll antenna size compared to green algae in which the expression cassette has not been introduced.

2. The method of claim 1, wherein the promoter is constitutive.

3. The method of claim 1, wherein the promoter is inducible.

4. The method of claim 1, wherein the polynucleotide is operably linked to the promoter in the antisense orientation.

5. The method of claim 1, wherein the polynucleotide is operably linked to the promoter in the sense orientation.

6. The method of claim 1, wherein the polynucleotide is an siRNA.

7. The method of claim 1, wherein the polynucleotide comprises at least 200 contiguous nucleotides of a nucleic acid that encodes SEQ ID NO:2.

8. The method of claim 1, wherein the nucleic acid that encodes SEQ ID NO:2 has the sequence set forth in SEQ ID NO:3 or SEQ ID NO:1.

9. The method of claim 1, wherein the algae are selected from *Chlamydomonas reinhardtii, Scenedesmus obliquus, Chlorella vulgaris, Botryococcus braunii, Botryococcus sudeticus, Dunaliella salina*, or *Haematococcus pluvialis*.

10. A strain of green algae comprising an expression cassette comprising a polynucleotide, or a complement thereof, that is at least 90% percent identical to at least 200 contiguous nucleotides of a sequence encoding SEQ ID NO:2; or comprises at least 20 contiguous nucleotides to SEQ ID NO:1 or SEQ ID NO:3, or the complement thereof.

11. The strain of green algae of claim 10, wherein the algae are selected from *Chlamydomonas reinhardtii, Scenedesmus obliquus, Chlorella vulgaris, Botryococcus braunii, Botryococcus sudeticus, Dunaliella salina*, or *Haematococcus pluvialis*.

12. A method of enhancing yields of photosynthetic productivity under high-density growth conditions, the method comprising cultivating a plant of claim 10 under bright sunlight and high density growth conditions.

13. The method of claim 1, wherein the polynucleotide is at least 90% identical to at least 200 contiguous nucleotides of a nucleic acid sequence encoding SEQ ID NO:2.

14. The method of claim 1, wherein the polynucletoide comprises at least 20 contiguous nucleotides of SEQ ID NO:1or SEQ ID NO:3, or the complement thereof.

15. The strain of green algae of claim 10, wherein the promoter is constitutive.

16. The strain of green algae of claim 10, wherein the promoter is inducible.

17. The strain of green algae of claim 10, wherein the polynucleotide is operably linked to the promoter in the antisense orientation.

18. The strain of green algae of claim 10, wherein the polynucleotide is operably linked to the promoter in the sense orientation.

19. The strain of green algae of claim 10, wherein the polynucleotide is an siRNA.

20. The strain of green algae of claim 10, wherein the polynucleotide is at least 90% percent identical to at least 200 contiguous nucleotides of a sequence encoding SEQ ID NO:2.

21. The strain of green algae of claim 10, wherein the polynucleotide comprises at least 200 contiguous nucleotides of a nucleic acid that encodes SEQ ID NO:2.

22. The strain of green algae of claim 20, wherein the nucleic acid that encodes SEQ ID NO:2 has the sequence set forth in SEQ ID NO:3 or SEQ ID NO:1.

23. The strain of green algae of claim 10, wherein the polynucleotide comprises at least 20 contiguous nucleotides of SEQ ID NO:1 or SEQ ID NO:3, or the complement thereof.

* * * * *

SEQUENCE LISTING

<160> NUMBER OF SEQ ID NOS: 33

<210> SEQ ID NO 1
<211> LENGTH: 2065
<212> TYPE: DNA
<213> ORGANISM: Chlamydomonas reinhardtii
<220> FEATURE:
<223> OTHER INFORMATION: truncated light-harvesting chlorophyll antenna
      size (Tla1) insertional mutant cDNA
<220> FEATURE:
<221> NAME/KEY: CDS
<222> LOCATION: (105)..(746)
<223> OTHER INFORMATION: Tla1

<400> SEQUENCE: 1

```
ggaacctcga tgtcgtgttg actttgcgtt acaaccgtga agtatattag aactcatttg      60
cctgccacaa cctcagacca agagacgcgc gaaaaactga cacg atg act ttc agc     116
                                                  Met Thr Phe Ser
                                                  1 tgc tcc gct gac caa acc gcg ctc tta aag att ctt gca cac gcg gct     164
Cys Ser Ala Asp Gln Thr Ala Leu Leu Lys Ile Leu Ala His Ala Ala
 5                  10                  15                  20 aag tat cca tca aat agc gtg aat ggt gtc ctc gtc ggg aca gcg aag     212
Lys Tyr Pro Ser Asn Ser Val Asn Gly Val Leu Val Gly Thr Ala Lys
             25                  30                  35 gag ggc ggc tct gtc gaa atc ctg gac gcg att cca ctg tgt cac acg     260
Glu Gly Gly Ser Val Glu Ile Leu Asp Ala Ile Pro Leu Cys His Thr
         40                  45                  50 acg ctg acc ctg gcg cca gca ctg gag ata ggt ctc gcc cag gtg gag     308
Thr Leu Thr Leu Ala Pro Ala Leu Glu Ile Gly Leu Ala Gln Val Glu
     55                  60                  65 tcc tac acg cat atc acg ggc agc gtg gcg att gtg ggc tac tac caa     356
Ser Tyr Thr His Ile Thr Gly Ser Val Ala Ile Val Gly Tyr Tyr Gln
 70                  75                  80 tca gac gca cgt ttc ggc ccc ggg gac cta ccc ccg cta ggt cgc aaa     404
Ser Asp Ala Arg Phe Gly Pro Gly Asp Leu Pro Pro Leu Gly Arg Lys
 85                  90                  95                 100
```

| | | | | | | | | | | | | | | | | |
|---|---|---|---|---|---|---|---|---|---|---|---|---|---|---|---|---|
| att | gcg | gac | aag | gtg | tct | gag | cac | cag | gct | cag | gcg | gtg | gtg | ctg | gtg | 452 |
| Ile | Ala | Asp | Lys 105 | Val | Ser | Glu | His | Gln 110 | Ala | Gln | Ala | Val | Val 115 | Leu | Val | |
| ctg | gac | aac | aag | cgg | ctg | gag | cag | ttc | tgc | aag | gcg | cag | gcg | gac | aac | 500 |
| Leu | Asp | Asn | Lys 120 | Arg | Leu | Glu | Gln | Phe 125 | Cys | Lys | Ala | Gln | Ala 130 | Asp | Asn | |
| ccg | ttc | gag | ctg | ttc | agc | aag | gat | ggc | agc | aag | ggt | tgg | aag | cgc | gcg | 548 |
| Pro | Phe | Glu | Leu 135 | Phe | Ser | Lys | Asp | Gly 140 | Ser | Lys | Gly | Trp | Lys 145 | Arg | Ala | |
| agc | gcc | gat | ggc | gga | gag | ctg | gcg | ctt | aaa | aac | gcg | gac | tgg | aag | aag | 596 |
| Ser | Ala | Asp | Gly 150 | Gly | Glu | Leu | Ala | Leu 155 | Lys | Asn | Ala | Asp | Trp 160 | Lys | Lys | |
| ctg | cgc | gag | gag | ttc | ttc | gtt | atg | ttc | aag | cag | ctg | aag | cac | cgg | aca | 644 |
| Leu 165 | Arg | Glu | Glu | Phe | Phe 170 | Val | Met | Phe | Lys | Gln 175 | Leu | Lys | His | Arg | Thr 180 | |
| ctc | cac | gat | ttt | gag | gag | cac | ctg | gac | gac | gcc | ggg | aaa | gac | tgg | ctc | 692 |
| Leu | His | Asp | Phe | Glu 185 | Glu | His | Leu | Asp | Asp 190 | Ala | Gly | Lys | Asp | Trp 195 | Leu | |
| aac | aag | ggc | ttc | gcc | tcc | tcg | gtc | aaa | ttc | ctg | ttg | ccc | ggc | aac | gcg | 740 |
| Asn | Lys | Gly | Phe | Ala 200 | Ser | Ser | Val | Lys | Phe 205 | Leu | Leu | Pro | Gly | Asn 210 | Ala | |
| ctg | taa | gggccgcgtg | aggctagccg | ggatggcggt | tccgcgggat | ggtcgcagtg | | | | | | | | | | 796 |
| Leu | | | | | | | | | | | | | | | | |

```
ccggggtgtg tgttgagagg aggagccggt gggggggaaa gaggttgagg aggtaggaga      856
gaggcgctgg catggaggcc gggaggcgct ggagctggag ctggcgagct ggtgggtggt      916
gctgggcgag atcctggagg cacaggagtg gtatgggcgg tgcagggaca gcgacagcgg      976
atcggcggac ggtattggtg gagggtgcgg gggccctggg gtagtgtgca gggtgtgtgc     1036
cacgtggctt gccgcaaagc gcagcgtacc gatagttgag agaaagcacc tgcggccctg     1096
cgcggccgcg gcgtggcggc gcgtggggac acgcgcatcg tgccgggtcg ccgcaggccg     1156
gagtgaattt cgtgctgcac ggcgcgttga ccagtccacc gactgacggc caacggccat     1216
gagggcttgt tttgggggat agggtcacat gacattttcg gcgttctttg cagtcagaat     1276
caggatacgc ttgctttagt cttgattgtc agacttgtca ggctgacgtt tcaggcagac     1336
gagagctcat gtggttttga ctaaccgggc gttgaccatg ggcagtccca acgtgccgt      1396
gccacagggc atagcgagtg ccatgtgctc tcgagggcga ggtcgtgagg cacgtggaaa     1456
ctgttgcggc gccttcacca tgggtgcttt ctcgcgtgag gcacgtgaaa ctgttgcggc     1516
gccttcacca tgggtgctct ctctcgtgag gctcagcggc aagtaccagg agggcgcaa      1576
gacacggatg aagcagtggt tgcgcatgcc gcggtctgtt ggccgccggg aggtgatcgg     1636
tgtgacgtgg ctggtgcgtg tggtggtttc tcccgtggcc tcccgtgtgt gactggtgcg     1696
tgtttgacgt ggcaaggtag gtaaatagta gtaaagcggc ccagatacgt tgctgtggcg     1756
gttgtgcgtg cgcaggtggt gcataggaca gcgttggttg tgtgtgcctg tgctgtgctg     1816
tgcggtgccg gaccgaagcg cggggcggac aggcgcaggg tggtagcggc gtggcgggta     1876
ggctgccgca cacagtacgt gtaactgtat gctgcgctgc atgttactct gcttacggat     1936
gcttcctgac tgtacgtgtg gtgcttgggt cgtgtcgccg tgcaacgctg ctggcggctt     1996
caatgggtgg ctgcggatca gtgggtggct gcgtgtatcg gcgcgcccgt gttgaatcga     2056
ggactgcag                                                            2065
```

<210> SEQ ID NO 2
<211> LENGTH: 213
<212> TYPE: PRT

```
<213> ORGANISM: Chlamydomonas reinhardtii
<220> FEATURE:
<223> OTHER INFORMATION: Tla1
<220> FEATURE:
<221> NAME/KEY: DOMAIN
<222> LOCATION: (9)..(33)
<223> OTHER INFORMATION: conserved Domain A
<220> FEATURE:
<221> NAME/KEY: DOMAIN
<222> LOCATION: (41)..(70)
<223> OTHER INFORMATION: conserved Domain B
<220> FEATURE:
<221> NAME/KEY: DOMAIN
<222> LOCATION: (75)..(129)
<223> OTHER INFORMATION: conserved Domain C
<220> FEATURE:
<221> NAME/KEY: DOMAIN
<222> LOCATION: (135)..(163)
<223> OTHER INFORMATION: conserved Domain D
<220> FEATURE:
<221> NAME/KEY: DOMAIN
<222> LOCATION: (177)..(200)
<223> OTHER INFORMATION: conserved Domain E

<400> SEQUENCE: 2

Met Thr Phe Ser Cys Ser Ala Asp Gln Thr Ala Leu Leu Lys Ile Leu
 1               5                  10                  15

Ala His Ala Ala Lys Tyr Pro Ser Asn Ser Val Asn Gly Val Leu Val
            20                  25                  30

Gly Thr Ala Lys Glu Gly Gly Ser Val Glu Ile Leu Asp Ala Ile Pro
        35                  40                  45

Leu Cys His Thr Thr Leu Thr Leu Ala Pro Ala Leu Glu Ile Gly Leu
    50                  55                  60

Ala Gln Val Glu Ser Tyr Thr His Ile Thr Gly Ser Val Ala Ile Val
65                  70                  75                  80

Gly Tyr Tyr Gln Ser Asp Ala Arg Phe Gly Pro Gly Asp Leu Pro Pro
                85                  90                  95

Leu Gly Arg Lys Ile Ala Asp Lys Val Ser Glu His Gln Ala Gln Ala
            100                 105                 110

Val Val Leu Val Leu Asp Asn Lys Arg Leu Glu Gln Phe Cys Lys Ala
        115                 120                 125

Gln Ala Asp Asn Pro Phe Glu Leu Phe Ser Lys Asp Gly Ser Lys Gly
    130                 135                 140

Trp Lys Arg Ala Ser Ala Asp Gly Gly Glu Leu Ala Leu Lys Asn Ala
145                 150                 155                 160

Asp Trp Lys Lys Leu Arg Glu Glu Phe Phe Val Met Phe Lys Gln Leu
                165                 170                 175

Lys His Arg Thr Leu His Asp Phe Glu Glu His Leu Asp Asp Ala Gly
            180                 185                 190

Lys Asp Trp Leu Asn Lys Gly Phe Ala Ser Ser Val Lys Phe Leu Leu
        195                 200                 205

Pro Gly Asn Ala Leu
    210

<210> SEQ ID NO 3
<211> LENGTH: 2181
<212> TYPE: DNA
<213> ORGANISM: Chlamydomonas reinhardtii
<220> FEATURE:
<223> OTHER INFORMATION: truncated light-harvesting chlorophyll antenna
      size (Tla1) insertional mutant genomic sequence

<400> SEQUENCE: 3
```

```
ggaacctcga tgtcgtgttg actttgcgtt acaaccgtga agtatattag aactcatttg    60
cctgccacaa cctcagacca agagacgcgc gaaaaactga cacgatgact ttcagctgct   120
ccgctgacca aaccgcgctc ttaaagattc ttgcacacgc ggctaagtat ccatcaaata   180
gcgtgaatgg tgtcctcgtc gggacagcga aggagggcgg ctctgtcgaa atcctggacg   240
cgattccact gtgtcacacg acgctgaccc tggcgccagc actggagata ggtctcgccc   300
aggtgcgcat ggccccgaga gcccggggcg tggcttgtgc tcgtcgatct gcgtgcatta   360
gttaccgcat cgctcccatg ctgcattccg cgctcagcct caaataccct gattgcaggt   420
ggagtcctac acgcatatca cgggcagcgt ggcgattgtg ggctactacc aatcagacgc   480
acgtttcggc cccggggacc taccccgct aggtcgcaaa attgcggaca aggtgtctga    540
gcaccaggct caggcggtgg tgctggtgct ggacaacaag cggctggagc agttctgcaa   600
ggcgcaggcg gacaacccgt tcgagctgtt cagcaaggat ggcagcaagg gttggaagcg   660
cgcgagcgcc gatggcggag agctggcgct taaaaacgcg gactggaaga gctgcgcga   720 ggagttcttc gttatgttca agcagctgaa gcaccggaca ctccacgatt ttgaggagca   780
cctggacgac gccgggaaag actggctcaa caagggcttc gcctcctcgg tcaaattcct   840
gttgcccggc aacgcgctgt aagggccgcg tgaggctagc cgggatggcg gttccgcggg   900
atggtcgcag tgccggggtg tgtgttgaga ggaggagccg gtgggggga aagaggttga    960 ggaggtagga gagaggcgct ggcatggagg ccgggaggcg ctggagctgg agctggcgag  1020
ctggtgggtg tgtgctgggcg agatcctgga ggcacaggag tggtatgggc ggtgcaggga  1080
cagcgacagc ggatcggcgg acggtattgg tggagggtgc gggggccctg gggtagtgtg  1140
cagggtgtgt gccacgtggc ttgccgcaaa gcgcagcgta ccgatagttg agagaaagca  1200
cctgcggccc tgcgcggccg cggcgtggcg gcgcgtgggg acacgcgcat cgtgccgggt  1260
cgccgcaggc cggagtgaat tcgtgctgc acggcgcgtt gaccagtcca ccgactgacg   1320
gccaacggcc atgagggctt gttttggggg ataggtcac atgacatttt cggcgttctt   1380
tgcagtcaga atcaggatac gcttgcttta gtcttgattg tcagacttgt caggctgacg   1440
tttcaggcag acgagagctc atgtggtttt gactaaccgg gcgttgacca tgggcagtcc   1500
caaacgtgcc gtgccacagg gcatagcgag tgccatgtgc tctcgagggc gaggtcgtga   1560
ggcacgtgga aactgttgcg gcgccttcac catgggtgct ttctcgcgtg aggcacgtga   1620
aactgttgcg gcgccttcac catgggtgct ctctctcgtg aggctcagcg gcaagtacca   1680
gggagggcgc aagacacgga tgaagcagtg gttgcgcatg ccgcggtctg ttggccgccg   1740
ggaggtgatc ggtgtgacgt ggctggtgcg tgtggtggtt ctcccgtgg cctcccgtgt    1800 gtgactggtg cgtgtttgac gtggcaaggt aggtaaaatag tagtaaagcg gcccagatac  1860
gttgctgtgg cggttgtgcg tgcgcaggtg gtgcatagga cagcgttggt tgtgtgtgcc  1920
tgtgctgtgc tgtgcggtgc cggaccgaag cgcggggcgg acaggcgcag ggtggtagcg  1980
gcgtggcggg taggctgccg cacacagtac gtgtaactgt atgctgcgct gcatgttact  2040
ctgcttacgg atgcttcctg actgtacgtg tggtgcttgg gtcgtgtcgc cgtgcaacgc  2100
tgctggcggc ttcaatgggt ggctgcggat cagtgggtgg ctgcgtgtat cggcgcgccc  2160
gtgttgaatc gaggactgca g                                             2181
```

<210> SEQ ID NO 4
<211> LENGTH: 21
<212> TYPE: DNA
<213> ORGANISM: Artificial Sequence

```
<220> FEATURE:
<223> OTHER INFORMATION: Description of Artificial Sequence:PCR "primer
      1", Tla1 5' UTR specific upstream primer

<400> SEQUENCE: 4
tacgggaatt tgcggaacct c                                             21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR "primer
      4", Tla1 Exon-2 specific reverse primer

<400> SEQUENCE: 5
ttgttgtcca gcaccagcac                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:PCR "primer
      7", pJD67 vector 3' end specific primer

<400> SEQUENCE: 6
caacgcatat agcgctagca gc                                            22

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:PCR "primer
      6", Tla1 3' UTR specific downstream primer

<400> SEQUENCE: 7
aacacacacc ccgcact                                                  17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:PCR "primer
      8", Ble (zeocin resistance) gene exon 2 specific
      forward primer

<400> SEQUENCE: 8
gggacttcgt ggaggacg                                                 18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:PCR "primer
      9", Ble (zeocin resistance) gene exon 3 specific
      reverse primer

<400> SEQUENCE: 9
ggttagtcct gctcctcgg                                                19

<210> SEQ ID NO 10
<211> LENGTH: 30
<212> TYPE: DNA
```

<213> ORGANISM: Artificial Sequence
<220> FEATURE:
<223> OTHER INFORMATION: Description of Artificial Sequence:RT-PCR
    "primer 3", T1a1 exon 1 specific upstream primer

<400> SEQUENCE: 10
gggcccttca gctgctccgc tgaccaaacc                                30

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:RT-PCR
    "primer 5", T1a1 coding sequence specific reverse primer

<400> SEQUENCE: 11
gggcccgaac gggttgtccg cctgcgcctt gc                             32

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:RT-PCR
    "primer 2", T1a1 5' UTR specific forward primer

<400> SEQUENCE: 12
gctgctccgc tgaccaaa                                             18

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:PCR
    amplification primer TCF, T1a1 5' end cloning
    primer

<400> SEQUENCE: 13
cggggtacca ctttcagctg ctccgct                                   27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:PCR
    amplification primer TCR, T1a1 3' end cloning
    primer

<400> SEQUENCE: 14
ccaagcttcc tctttccccc ccacc                                     25

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:PCR "primer
    1", T1a1 5' UTR specific upstream primer

<400> SEQUENCE: 15
gcctgccaca acctcagacc aagagacg                                  28

<210> SEQ ID NO 16
<211> LENGTH: 372

```
<212> TYPE: DNA
<213> ORGANISM: Artificial Sequence
<220> FEATURE:
<223> OTHER INFORMATION: Description of Artificial Sequence:DNA sequence
      obtained from 5' RACE of wild type (cw15)

<400> SEQUENCE: 16
gatgtcgtgt tgactttgcg ttacaaccgt gaagtatatt agaactcatt tgcctgccac     60
aacctcagac caagagacgc gcgaaaaact gacacgatga ctttcagctg ctccgctgac    120
caaaccgcgc tcttaaagat tcttgcacac gcggctaagt atccatcaaa tagcgtgaat    180
ggtgtcctcg tcgggacagc gaaggagggc ggctctgtcg aaatcctgga cgcgattcca    240
ctgtgtcaca cgacgctgac cctggcgcca gcactggaga taggtctcgc ccaggtggag    300
tcctacacgc atatcacggg cagcgtggcg attgtgggct actaccaatc agacgcacgt    360
ttcggccccg gg                                                        372

<210> SEQ ID NO 17
<211> LENGTH: 463
<212> TYPE: DNA
<213> ORGANISM: Artificial Sequence
<220> FEATURE:
<223> OTHER INFORMATION: Description of Artificial Sequence:DNA sequence
      obtained from 5' RACE of tla mutant

<400> SEQUENCE: 17
acgccatagt gactggcgat gctgtcggaa tggacgatat cccgcaagag gcccggcagt     60
accggcataa ccaagcctat gcctacagca tccagggtga cggtgccgag gatgacgatg    120
agcgcattgt tagattccat acacggtgcc tgactgcgtt agcaatttaa ctgtgataaa    180
ctaccgcatg actttcagct gctccgctga ccaaaccgcg ctcttaaaga ttcttgcaca    240
cgcggctaag tatccatcaa atagtgtgaa tggtgtcctc gtcgggacag cgaaggaggg    300
cggctctgtc gaaatcctgg acgcgattcc actgtgtcac acgacgctga ccctggcgcc    360
agcactggag ataggtctcg cccaggtgga gtcctacacg catatcacgg gcagcgtggc    420
gattgtgggc tactaccaat cagacgcacg tttcggcccc ggg                      463

<210> SEQ ID NO 18
<211> LENGTH: 580
<212> TYPE: DNA
<213> ORGANISM: Artificial Sequence
<220> FEATURE:
<223> OTHER INFORMATION: Description of Artificial Sequence:3' end DNA
      sequence of plasmid pJD67

<400> SEQUENCE: 18
cggcaccagc aagcgctcgg tgctggagca ggtgcagaag atgcgcacct acctggcggc     60
ggagggacag cactgagcgg gtcgggggag gggggcgggt gtgtatgtg tgtgtgtgtg    120 cgtgtgtaag tctcggtgga ggggtggtcc tctatatggc ggcggggcca cagggggacg    180
ggtgtgacag agttacggcc ggagccagcg gagtcccggg atggattaag gatccacagg    240
acgggtgtgg tcgccatgat cgcgtagtcg atagtggctc caagtagcga agcgagcagg    300
actgggcggc ggccaaagcg gtcggacagt gctccgagaa cgggtgcgca tagaaattgc    360
atcaacgcat atagcgctag cagcacgcca tagtgactgg cgatgctgtc ggaatggacg    420
atatcccgca agaggcccgg cagtaccggc ataaccaagc ctatgcctac agcatccagg    480
gtgacggtgc cgaggatgac gatgagcgca ttgttagatt tcatacacgg tgcctgactg    540
cgttagcaat ttaactgtga taaactaccg cattaaagct                          580
```

```
<210> SEQ ID NO 19
<211> LENGTH: 208
<212> TYPE: PRT
<213> ORGANISM: Arabidopsis thaliana
<220> FEATURE:
<223> OTHER INFORMATION: Tla-like protein from Arabidopsis thaliana

<400> SEQUENCE: 19

Met Gly Met Gly Ser Asn Gly Glu Leu Lys Tyr Glu Ile Ser Gln Asn
 1               5                  10                  15

Ala Tyr Ile Lys Leu Val Leu His Ser Leu Arg His Lys Thr Ala Ala
            20                  25                  30

Val Asn Gly Val Leu Val Gly Arg Ile Ser Pro Lys Asp Asp Gly Val
        35                  40                  45

Val Glu Ile Ser Asp Ser Val Pro Leu Phe His Ser Asn Leu Ala Leu
    50                  55                  60

Leu Pro Pro Leu Glu Ile Ser Leu Ile Met Ile Glu Glu His Tyr Val
65                  70                  75                  80

Ala Gln Gly Leu Ser Ile Val Gly Tyr Phe His Ala Asn Glu Arg Phe
                85                  90                  95

Asp Asp Val Glu Leu Cys Gly Val Ala Lys Asn Ile Gly Asp His Ile
            100                 105                 110

Ser Arg Tyr Phe Pro Gln Ala Pro Ile Leu Leu Leu Asn Asn Lys Lys
        115                 120                 125

Leu Glu Ala Leu Ser Lys Gly Lys Glu Arg Ser Pro Val Met Gln Leu
    130                 135                 140

Cys Val Lys Asp Ala Ser Lys Asn Trp Arg Val Val Gly Ala Asp Gly
145                 150                 155                 160

Gly Ser Lys Leu Leu Leu Lys Glu Pro Ser Ala Asn Val Val Leu Ser
                165                 170                 175

Asp Tyr Ile Ser Ser Glu Lys Trp Lys Asp Val Thr Asp Val Asp Asp
            180                 185                 190

His Leu Asp Asp Val Thr Lys Asp Trp Leu Asn Pro Gly Leu Phe Asn
        195                 200                 205

<210> SEQ ID NO 20
<211> LENGTH: 209
<212> TYPE: PRT
<213> ORGANISM: Oryza sativa
<220> FEATURE:
<223> OTHER INFORMATION: Tla-like protein from Oryza sativa

<400> SEQUENCE: 20

Met Gly Ala Glu Cys Lys Tyr Glu Val Ala Gln Val Ala Tyr Val Lys
 1               5                  10                  15

Leu Ala Leu His Ala Leu Lys His Pro Ala Ala Val Asn Gly Leu
            20                  25                  30

Leu Val Gly Arg Leu Leu Asp Gly Ala Ala Ser Pro Ala Ala Val Val
        35                  40                  45

Ser Ile Ala Asp Ala Val Pro Leu Ser His His Pro His His Leu Pro
    50                  55                  60

Leu Leu Pro Thr Leu Glu Leu Ala Leu Thr Leu Val Glu Asp His Phe
65                  70                  75                  80

Ala Ala Gln Gly Leu Ala Val Val Gly Tyr Tyr His Ala Asn Ala Arg
                85                  90                  95

Arg Asp Asp Ala Asp Leu Pro Pro Val Ala Lys Arg Val Gly Asp His
```

```
                    100                 105                 110
Val Phe Arg Asn Phe Pro Arg Ala Ala Val Leu Leu Leu Asp Asn Lys
                115                 120                 125
Lys Leu Glu Glu Ala Val Lys Gly Lys Ser Arg Glu Pro Val Val Gln
            130                 135                 140
Leu Tyr Thr Arg Asp Ser Ser Lys Ser Trp Arg Gln Ala Gly Ser Asp
145                 150                 155                 160
Gly Ser Ser Gln Leu Thr Leu Lys Glu Pro Ser Thr Asn Met Val Leu
                165                 170                 175
Ala Asp His Val Thr Thr Lys Lys Trp Gln Gln Val Val Asp Phe Asp
                180                 185                 190
Asp His Leu Asp Asp Ile Ser Lys Asp Trp Leu Asn Pro Gly Leu Leu
                195                 200                 205
Ala
```

```
<210> SEQ ID NO 21
<211> LENGTH: 208
<212> TYPE: PRT
<213> ORGANISM: Homo sapiens
<220> FEATURE:
<223> OTHER INFORMATION: Tla-like protein human CGI 112 protein

<400> SEQUENCE: 21

Met Gly Glu Val Glu Ile Ser Ala Leu Ala Tyr Val Lys Met Cys Leu
1               5                   10                  15
His Ala Ala Arg Tyr Pro His Ala Ala Val Asn Gly Leu Phe Leu Ala
                20                  25                  30
Pro Ala Pro Arg Ser Gly Glu Gly Leu Cys Leu Thr Asp Cys Val Pro
            35                  40                  45
Leu Phe His Ser His Leu Ala Leu Ser Val Met Leu Glu Val Ala Leu
50                  55                  60
Asn Gln Val Asp Val Trp Gly Ala Gln Ala Gly Leu Val Val Ala Gly
65                  70                  75                  80
Tyr Tyr His Ala Asn Ala Ala Val Asn Asp Gln Ser Pro Gly Pro Leu
                85                  90                  95
Ala Leu Lys Ile Ala Gly Arg Ile Ala Glu Phe Phe Pro Asp Ala Val
                100                 105                 110
Leu Ile Met Leu Asp Asn Gln Lys Leu Val Pro Gln Pro Arg Val Pro
                115                 120                 125
Pro Val Ile Val Leu Glu Asn Gln Gly Leu Arg Trp Val Pro Lys Asp
            130                 135                 140
Lys Asn Leu Val Met Trp Arg Asp Trp Glu Glu Ser Arg Gln Met Val
145                 150                 155                 160
Gly Ala Leu Leu Glu Asp Arg Ala His Gln His Leu Val Asp Phe Asp
                165                 170                 175
Cys His Leu Asp Asp Ile Arg Gln Asp Trp Thr Asn Gln Arg Leu Asn
                180                 185                 190
Thr Gln Ile Thr Gln Trp Val Gly Pro Thr Asn Gly Asn Gly Asn Ala
                195                 200                 205
```

```
<210> SEQ ID NO 22
<211> LENGTH: 203
<212> TYPE: PRT
<213> ORGANISM: Drosophila melanogaster
<220> FEATURE:
<223> OTHER INFORMATION: Tla-like protein from Drosophila melanogaster
```

<400> SEQUENCE: 22

```
Met Cys Asp Tyr Lys Val Ser Glu Arg Ala Tyr Ala Lys Leu Ile Phe
  1               5                  10                  15

His Ala Ala Lys Tyr Pro His Gln Ala Val Asn Gly Leu Leu Leu Ala
             20                  25                  30

Glu Lys Thr Ser Lys Gly Ser Gln Val Glu Ile Val Asp Ala Ile Pro
         35                  40                  45

Leu Phe His Gln Cys Leu Tyr Val Thr Pro Met Ala Glu Val Ala Leu
     50                  55                  60

Met Leu Ile Asp Ala His Ala Glu Arg Glu Gly Leu Val Ile Ala Gly
 65                  70                  75                  80

Tyr Tyr Ala Ala Pro Glu Asn Phe Tyr Asp Asn Gln Val Asp Lys Thr
                 85                  90                  95

Pro Ala Ala Lys Ile Ala Asp Lys Ile Gln Glu Asn Phe Lys Asn Ala
            100                 105                 110

Cys Phe Val Val Val Asp Asn Lys Leu Met Thr Leu Gln His Asp Arg
        115                 120                 125

Ala Ala Ile Gln Val Phe Asn Cys Pro Gly Asp Ser Gly Ala Arg Trp
130                 135                 140

Ser Lys Ala Lys Phe Thr Leu Ser Gln Ala Ser Asp Thr Leu Glu Gly
145                 150                 155                 160

Val Ser Leu Leu Leu Lys Arg Gly Ala Met Arg Asp Leu Val Asp Phe
                165                 170                 175

Asp Asn His Leu Asp Asn Pro Asp Lys Asn Trp Thr Asn Asp Phe Leu
            180                 185                 190

Asn Gln Pro Leu Asn Asp Leu Gln Lys Leu Tyr
        195                 200
```

<210> SEQ ID NO 23
<211> LENGTH: 210
<212> TYPE: PRT
<213> ORGANISM: Zea mays
<220> FEATURE:
<223> OTHER INFORMATION: Tla-like protein from Zea mays

<400> SEQUENCE: 23

```
Met Gly Ala Glu Cys Arg Tyr Glu Val Ala Gln Ala Ala Tyr Ile Lys
  1               5                  10                  15

Leu Ala Leu His Ala Leu Lys His Pro Ala Thr Ala Val Asn Gly Leu
             20                  25                  30

Leu Val Gly Arg Leu Val Glu Pro Ser Ser Pro Ala Val Val Ser
         35                  40                  45

Val Ile Asp Ala Val Pro Leu Ser His His Pro His Leu Pro Leu
     50                  55                  60

Leu Pro Thr Leu Glu Leu Ala Leu Thr Leu Val Glu Asp His Phe Ala
 65                  70                  75                  80

Thr Gln Gly Glu Gly Leu Ala Val Val Gly Tyr Tyr His Ala Asn Pro
                 85                  90                  95

Arg Cys Asp Asp Thr Glu Leu Pro Pro Val Ala Lys Arg Val Gly Asp
            100                 105                 110

His Ile Phe Arg Tyr Phe Pro Arg Ser Ala Val Leu Leu Val Asp Asn
        115                 120                 125

Lys Lys Leu Glu Glu Ala Val Lys Gly Lys Phe Ser Asp Ala Val Ile
130                 135                 140

Gln Leu His Thr Arg Asp Ser Ser Lys Ser Trp Arg Gln Ala Gly Ser
```

```
                145                 150                 155                 160
Asp Gly Ser Ser Gln Leu Ile Leu Lys Glu Pro Ser Thr Asn Val Val
                    165                 170                 175

Leu Ala Asp His Val Thr Thr Lys Lys Trp Glu Lys Ile Val Asp Phe
            180                 185                 190

Asp Asp His Leu Asp Asp Ile Ser Lys Asp Trp Ser Asn Pro Gly Leu
        195                 200                 205

Leu Asp
    210

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence:Tla1 protein
      conserved domain, Chlamydomonas reinhardtii Domain
      A amino acid positions 9-33

<400> SEQUENCE: 24

Gln Thr Ala Leu Leu Lys Ile Leu Ala His Ala Ala Lys Tyr Pro Ser
1               5                   10                  15

Asn Ser Val Asn Gly Val Leu Val Gly
            20                  25

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence:Tla1 protein
      conserved domain, Chlamydomonas reinhardtii Domain
      B amino acid positions 41-70, hydrophobic domain

<400> SEQUENCE: 25

Val Glu Ile Leu Asp Ala Ile Pro Leu Cys His Thr Thr Leu Thr Leu
1               5                   10                  15

Ala Pro Ala Leu Glu Ile Gly Leu Ala Gln Val Glu Ser Tyr
            20                  25                  30

<210> SEQ ID NO 26
<211> LENGTH: 55
<212> TYPE: PRT
<213> ORGANISM: Artificial Sequence
<220> FEATURE:
<223> OTHER INFORMATION: Description of Artificial Sequence:Tla1 protein
      conserved domain, Chlamydomonas reinhardtii Domain
      C amino acid positions 75-129

<400> SEQUENCE: 26

Gly Ser Val Ala Ile Val Gly Tyr Tyr Gln Ser Asp Ala Arg Phe Gly
1               5                   10                  15

Pro Gly Asp Leu Pro Pro Leu Gly Arg Lys Ile Ala Asp Lys Val Ser
            20                  25                  30

Glu His Gln Ala Gln Ala Val Val Leu Val Leu Asp Asn Lys Arg Leu
        35                  40                  45

Glu Gln Phe Cys Lys Ala Gln
    50                  55

<210> SEQ ID NO 27
<211> LENGTH: 29
<212> TYPE: PRT
<213> ORGANISM: Artificial Sequence
```

```
<220> FEATURE:
<223> OTHER INFORMATION: Description of Artificial Sequence:Tla1 protein
      conserved domain, Chlamydomonas reinhardtii Domain
      D amino acid positions 135-163

<400> SEQUENCE: 27

Glu Leu Phe Ser Lys Asp Gly Ser Lys Gly Trp Lys Arg Ala Ser Ala
 1               5                  10                  15

Asp Gly Gly Glu Leu Ala Leu Lys Asn Ala Asp Trp Lys
             20                  25

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence:Tla1 protein
      conserved domain, Chlamydomonas reinhardtii Domain
      E amino acid positions 177-200

<400> SEQUENCE: 28

Lys His Arg Thr Leu His Asp Phe Glu Glu His Leu Asp Asp Ala Gly
 1               5                  10                  15

Lys Asp Trp Leu Asn Lys Gly Phe
             20

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence:nucleic acid
      sequence example encoding amino acid sequence in
      reading frame

<400> SEQUENCE: 29
atgatggagc atcat                                                  15

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:amino acid
      sequence example encoded by nucleic acid sequence
      reading frame

<400> SEQUENCE: 30

Met Met Glu His His
 1               5

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:PCR "primer
      6", Tla1 3' UTR specific downstream primer

<400> SEQUENCE: 31
aacacacacc ccggcact                                               18

<210> SEQ ID NO 32
<211> LENGTH: 26
<212> TYPE: DNA
<213> ORGANISM: Artificial Sequence
<220> FEATURE:
```

-continued

```
<223> OTHER INFORMATION: Description of Artificial Sequence:PCR
      amplification primer TCR, Tla1 3' end cloning
      primer

<400> SEQUENCE: 32
cccaagcttc ctctttcccc cccacc                                          26

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:6* His tag

<400> SEQUENCE: 33

His His His His His His
  1               5
```